(12) United States Patent
Lathrop et al.

(10) Patent No.: US 7,789,194 B2
(45) Date of Patent: Sep. 7, 2010

(54) ACOUSTIC ATTENUATION CHAMBER

(75) Inventors: Raymond Lathrop, Northridge, CA (US); Leslie Hoffman, Tarzana, CA (US)

(73) Assignee: Cardinal Health 212, Inc., San Diego, CA (US)

( * ) Notice: Subject to any disclaimer, the term of this patent is extended or adjusted under 35 U.S.C. 154(b) by 493 days.

(21) Appl. No.: 11/788,624

(22) Filed: Apr. 20, 2007

(65) Prior Publication Data

US 2008/0257346 A1    Oct. 23, 2008

(51) Int. Cl.
*F01N 13/00*    (2010.01)
(52) U.S. Cl. .................. 181/225; 181/212; 181/222; 181/224; 181/252; 181/256
(58) Field of Classification Search .................. 181/212, 181/222, 252, 256, 224, 230, 286, 284, 291; 128/204.17
See application file for complete search history.

(56) References Cited

U.S. PATENT DOCUMENTS

| | | | |
|---|---|---|---|
| 2,541,159 A * | 2/1951 | Geiger | 181/208 |
| 3,642,093 A * | 2/1972 | Schach | 181/239 |
| 3,734,234 A | 5/1973 | Wirt | |
| 3,834,682 A | 9/1974 | McPhee | |
| 4,589,516 A * | 5/1986 | Inoue et al. | 181/256 |
| 5,728,980 A * | 3/1998 | Zarnick | 181/224 |
| 5,841,080 A * | 11/1998 | Iida et al. | 181/225 |
| 6,158,082 A * | 12/2000 | Beckey et al. | 15/326 |
| 6,385,321 B1 * | 5/2002 | Krueger et al. | 381/71.7 |
| 6,457,553 B1 * | 10/2002 | Goplen et al. | 181/272 |
| 7,195,014 B2 | 3/2007 | Hoffman | |
| 2004/0050618 A1 * | 3/2004 | Marocco | 181/248 |
| 2005/0166921 A1 | 8/2005 | Devries et al. | |
| 2008/0066751 A1 * | 3/2008 | Polacsek | 128/204.17 |

* cited by examiner

*Primary Examiner*—Jeffrey Donels
*Assistant Examiner*—Forrest M Phillips

(57) ABSTRACT

A silencer for a CPAP device comprises a housing assembly defining a flow path passing therethrough and including at least one of an inlet chamber, an acoustic chamber and a blower chamber. Each of the chambers has an inlet and an outlet for fluid communication therebetween. The silencer includes a combination of reactive components, resonators and dissipative elements disposed within the inlet, acoustic and blower chambers. The reactive component may be configured as a compliant-walled reactive tube. The resonator may be configured as a perforated plate defining a cavity volume. The dissipative element may comprise porous material substantially occupying the cavity volume bounded by the perforated plate in the chamber walls.

22 Claims, 12 Drawing Sheets

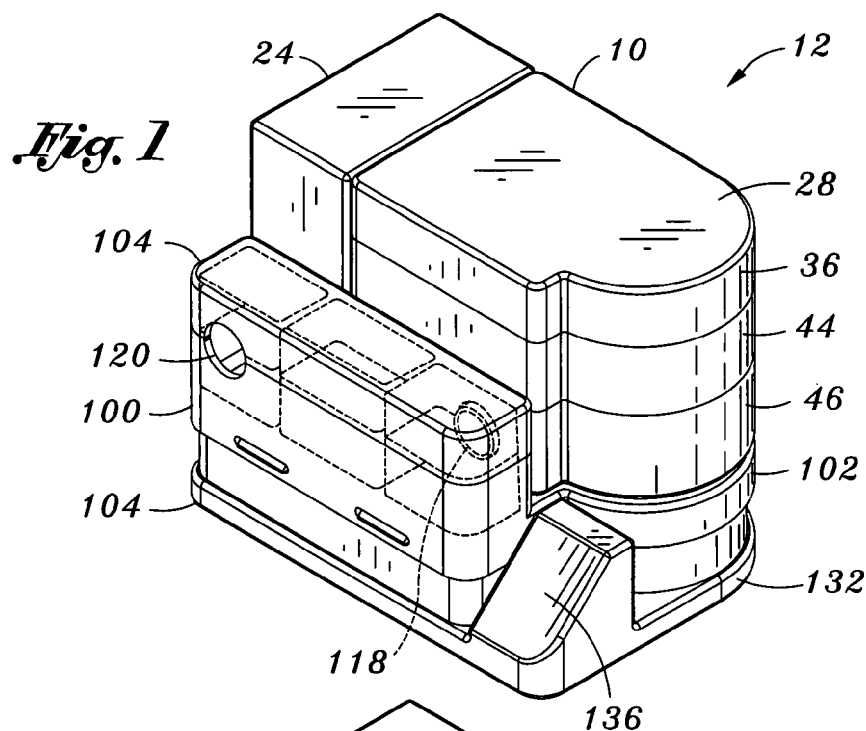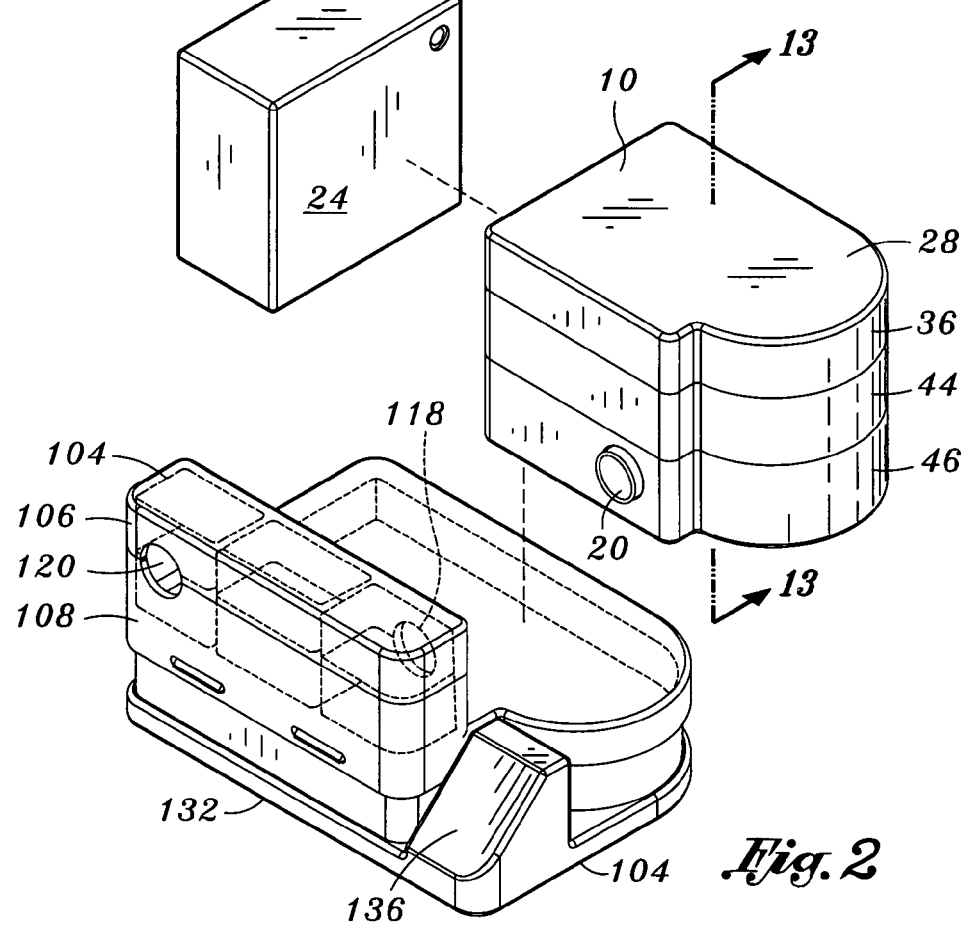

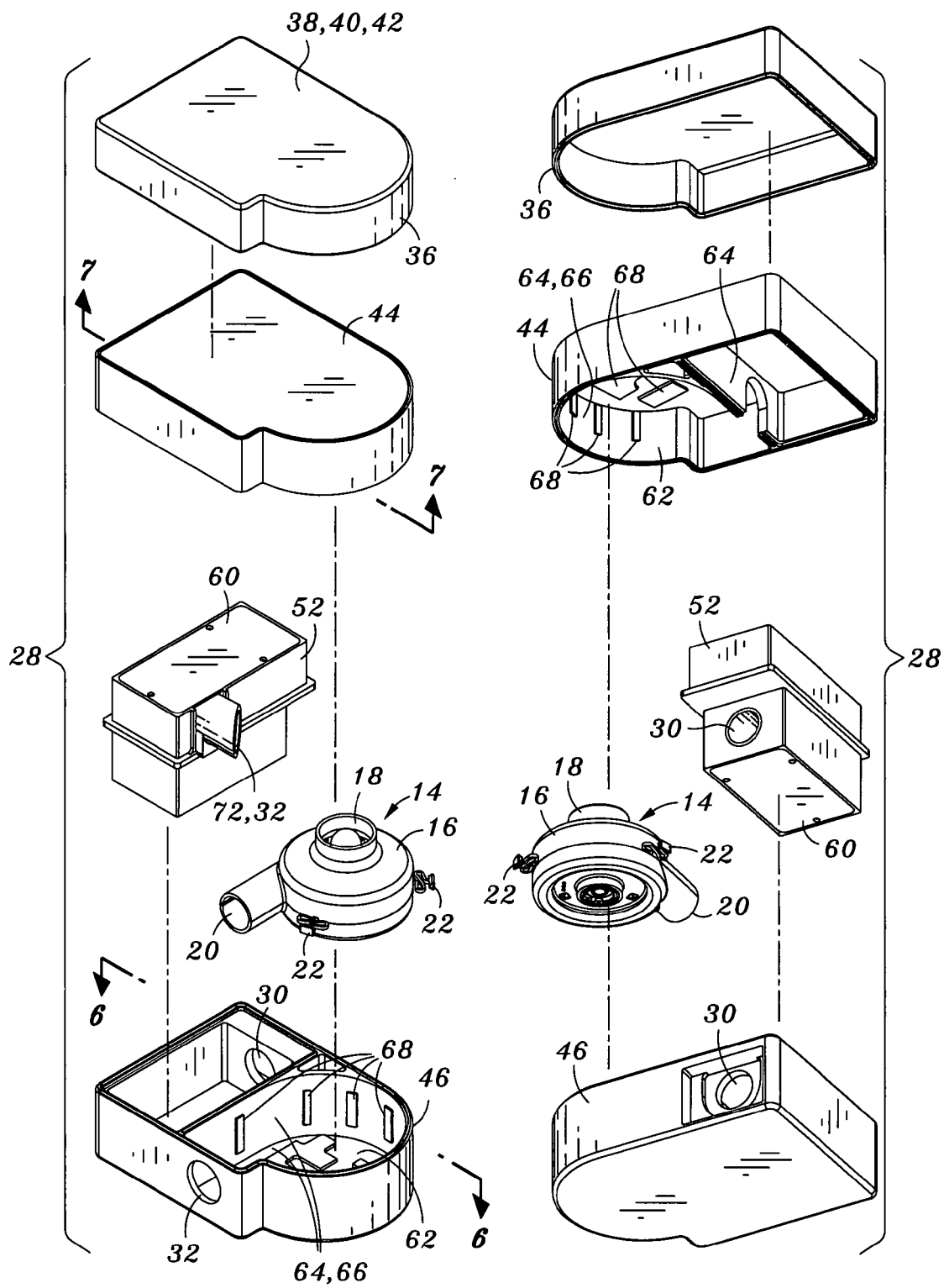

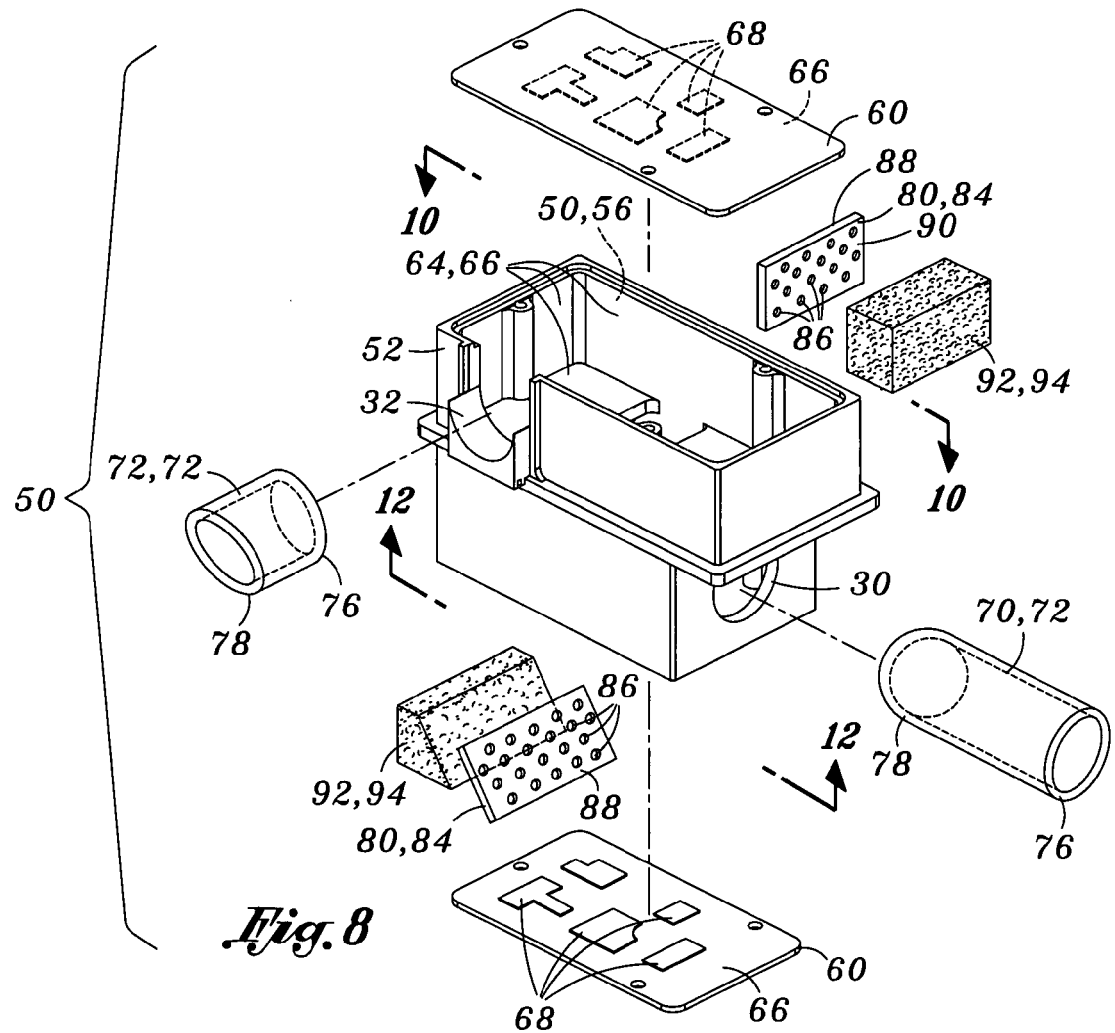
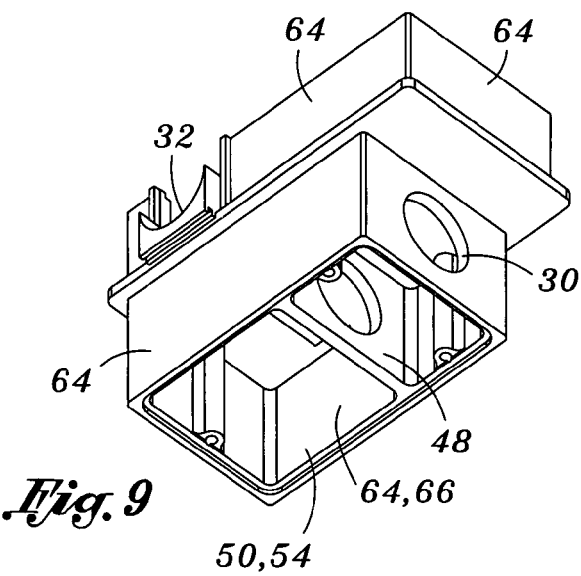

ACOUSTIC ATTENUATION CHAMBER

CROSS-REFERENCE TO RELATED APPLICATIONS

The present application is related to commonly-owned U.S. Pat. No. 7,195,014 entitled PORTABLE CONTINUOUS POSITIVE AIRWAY PRESSURE SYSTEM filed on May 13, 2005, and to commonly-owned U.S. Utility patent application Ser. No. 11/649,674 entitled USER INTERFACE AND HEAD GEAR FOR A CONTINUOUS POSITIVE AIRWAY PRESSURE DEVICE filed on Jan. 4, 2007, and commonly-owned U.S. Utility patent application Ser. No. 11/787,678 entitled CONTINUOUS POSITIVE AIRWAY PRESSURE DEVICE AND CONFIGURATION FOR EMPLOYING SAME, filed on Apr. 17, 2007, the entire contents of each patent and application being incorporated by reference herein.

STATEMENT RE: FEDERALLY SPONSORED RESEARCH/DEVELOPMENT (Not Applicable)

BACKGROUND

The present invention relates generally to patient ventilation systems and, more particularly, to a passive silencer as may be used with a blower assembly for a continuous positive airway pressure (CPAP) device. The passive silencer is specifically adapted to reduce the transmission of noise to ambient. CPAP noise includes mechanical noise generated by the rotating components of the blower assembly and air movement noise generated by the passage of air into and through the blower assembly.

One of the most common complaints of CPAP devices and one of the contributors to non-compliance with prescribed CPAP therapy is the excessive noise levels generated by conventional CPAP devices. Such noise is generally unpleasant and objectionable when experienced for extended periods of time. In certain environments such as in an intensive care unit (ICU) of a hospital, the relatively high sound levels generated by conventional CPAP devices is particularly noticeable and can increase anxiety in patients and family members and can affect the mood and concentration of healthcare workers.

Noise-induced stress can have a detrimental effect on the recovery of patients undergoing CPAP treatment. Some studies suggest that noise produced by conventional CPAP devices in a hospital setting may qualify as a health hazard in that the high sound levels can prolong recovery time. Although daytime ambient sound levels are relatively high and can mask some of the noise generated by conventional CPAP devices, such noise is particularly noticeable at night when ambient sound levels are reduced. Depending upon the hearing sensitivity, medication level and cultural background of the particular patient, noise generated by some CPAP devices can interrupt the patient's sleep or prevent sleep altogether.

The Environmental Protection Agency (EPA) and the World Health Organization both recommend maximum noise limits for hospitals of 40 to 45 decibels (dB) during the day and 35 dB at night. However, many conventional CPAP devices generate noise levels that are much higher than EPA recommendations. Recognizing this problem, several devices have been developed which attempt to reduce the objectionable sound levels produced by prior art CPAP devices. For example, commonly-owned U.S. Pat. No. 7,012,346 entitled Miniaturized Electric Motor and issued to Hoffman et al. discloses a motor blower unit for use in a CPAP device.

The motor blower unit is specifically adapted to operate with reduced noise output and includes an impeller mounted on a motor shaft of a motor assembly. The impeller is rotatably coupled to the motor assembly by a bearing assembly. The bearing assembly is sized and configured to minimize the level of mechanical noise produced during rotation of the motor assembly. The impeller is also constructed in a manner that minimizes vibration resulting from static and dynamic imbalances in the motor assembly.

Although the motor assembly is effective in minimizing mechanical noise output that is otherwise transmitted to ambient, a large portion of CPAP-generated noise is a result of air movement into and through the blower assembly. Furthermore, because air movement noise is generally broadband in nature as compared to the generally single-frequency or narrowband nature of mechanical noise, air movement noise is generally more difficult to attenuate.

As can be seen, there exists a need in the art for a CPAP device that reduces the amount of noise that is transmitted to the environment. Furthermore, there exists a need in the art for a CPAP device capable of generating reduced noise levels without a noticeable loss in operating efficiency. More particularly, there exists a need in the art for a CPAP device that reduces noise generated by air movement and which is capable of producing pressurized gas for delivery to the patient at normal pressure settings (e.g., 15-20 cm $H_2O$) and at maximum flow settings (e.g., 80 LPM). Finally, there exists a need in the art for a CPAP device with minimal noise output and which is small in size and simple in construction.

BRIEF SUMMARY

The present invention specifically addresses and alleviates the above-referenced deficiencies associated with conventional CPAP devices and other ventilation systems of the prior art. In one embodiment, a passive silencer is specifically adapted to attenuate air movement noise generated by a blower device for CPAP therapy. The blower device includes a motor blower unit for drawing in and compressing air for subsequent delivery to a patient. The silencer is disposed on a blower inlet side of the motor blower unit and is adapted to attenuate noise generated during operation of the motor blower unit.

The silencer includes a housing assembly having at least one of an inlet chamber, an acoustic chamber and a blower chamber each enclosed by chamber walls and each having an inlet, an outlet and defining a flow path therebetween. The silencer includes a combination of noise attenuating including reactive components, resonators and dissipative elements that are disposed throughout the inlet chamber, acoustic chamber and blower chamber. The reactive component may comprise a compliant-walled reactive tube mounted in the inlet chamber. The compliant or flexible nature of the wall of the reactive tube allows the use of space around the reactive tube to act as a resonator.

In one embodiment, the silencer may include a pair of perforated plates disposed on opposed longitudinal sides of the reactive tube and being position in spaced relation to the tube. Each one of the perforated plates may include a plurality of apertures formed therethrough. The inlet chamber may further include dissipative elements in order to further absorb acoustic energy. For example, the perforated plates may include porous material disposed behind the perforated plate in order to lower the quality factor (Q) of the inlet chamber. In this regard, the porous material fills a portion of the volume collectively defined by the perforated plate and the chamber walls and therefore increases the dissipative capability and broadens the attenuation bandwidth of the inlet chamber.

The acoustic chamber may be fluidly connected to the inlet chamber and may be configured as a reactive chamber including one or several perforated plate resonators oriented at an angle to the acoustic velocity. In this manner, the perforated plates produce a grazing flow with the acoustic velocity which increases resonator losses. The perforated plates in the acoustic chamber may be backed by dissipative elements in the form of porous material (i.e., open-cell foam) filling the volume therebehind. Regarding the construction of the perforated plates, the housing assembly may comprise a plurality of perforated plate resonators each having a plurality of apertures of uniform size (i.e., diameter) extending through a plate thickness of the perforated plates.

To simplify manufacturing and acoustic analysis, each of the perforated plates is preferably formed of the same material and at a particular plate thickness such that all of the perforated plates exhibit the same bending characteristics (i.e., stiffness). For purposes of simplifying vibration and acoustic analysis of the silencer in general and the attenuation properties of the perforated plates in particular, all the apertures in any perforated plate are preferably of uniform size (i.e., diameter) throughout the perforated plate. However, each of the perforated plates may include apertures that are of a different size than the apertures in any other perforated plate. In this manner, each perforated plate may be specifically tuned to attenuate a different frequency band as compared to the attenuation properties of any of the other attenuation features (e.g., reactive components, resonators and dissipative elements) disposed throughout the silencer.

In one embodiment, the acoustic chamber may be divided into first and second chambers. The first chamber may include one of the perforated plates which is preferably, but optionally, disposed in angled orientation to the acoustic flow and preferably, but optionally, having dissipative porous material (i.e., foam) disposed in the volume behind the perforated plate. The second chamber is fluidly connected to the first chamber and may include a second reactive tube extending into the blower chamber and therefore defining a space or cavity volume around the reactive tube. As in the first reactive tube in the inlet chamber, the second reactive tube is also preferably a compliant-walled tube such that the cavity volume surrounding the tube may act as a resonator. The second chamber may further include a perforated plate resonator optionally having foam disposed therebehind in order to provide energy-absorbing attenuation.

In one embodiment, the inlet chamber and the acoustic chamber may be incorporated into an acoustic housing which may be configured to be separably mounted with the housing assembly. The acoustic housing is preferably sized and configured such that when mounted in the housing assembly, housing gaps are formed between the exterior walls of the acoustic housing and the interior surfaces of the housing assembly. In this manner, structure-borne vibration generated by air flow passing through the acoustic housing is isolated from the housing assembly (e.g., CPAP enclosure). To further isolate structure-borne vibration, the acoustic housing may be mounted on a plurality of suspension members configured as serpentine spring members integrally molded into the sides of the acoustic housing in order to better isolate and attenuate vibration.

The motor blower unit may also be suspended in the blower chamber by means of a plurality of suspension mounts extending laterally outwardly from a blower housing. In this manner, the suspension mounts act as vibration isolators preventing mechanical vibration and air movement vibration from propagating to the housing assembly. The blower chamber may further include a perforated plate resonator backed by dissipative elements (e.g., porous material such as open-cell foam) to further attenuate air movement noise. The chamber walls of the inlet chamber, acoustic chamber and blower chamber may further include a plurality of randomly-placed thick sections which are specifically configured to prevent vibration of the chamber wall at a single low frequency resonance. The locally thick sections instead induce multiple higher-frequency resonances of lower amplitude in the chamber walls.

The flow path along the inlet chamber, acoustic chamber and blower chamber preferably defines a complex curved path with no line-of-sight from the reactive tube at the blower chamber to the reactive tube at inlet chamber. By providing a curved flow path with directional changes, additional broadband attenuation of acoustic energy is provided. Each of the reactive tubes is preferably sized and configured to minimize the velocity of the flow passing therethrough. In this manner, the reactive tubes prevent the flow from adversely affecting the attenuation capabilities of the silencer. The cross sectional area of the reactive tubes is preferably such that the flow velocity is maintained at less than about Mach 0.1 in order to optimize attenuation capability. The reactive tubes may be provided in different lengths to attenuate differing frequency bands. The trailing ends of the reactive tubes are also preferably angled or beveled in order to widen the attenuation bandwidth.

In a further embodiment, a humidifier assembly may be included with the blower device. The humidifier assembly comprises a reservoir which includes a container and a cover assembly which is engageable to the container. The reservoir is adapted for containing liquid such as water and is preferably transparent to allow viewing of the level of the liquid (i.e., water). The cover assembly has a humidifier inlet and a humidifier outlet. The humidifier inlet is preferably in fluid communication with the outlet of the housing assembly such that pressurized gas generated by the blower assembly is forced into the humidifier inlet whereupon vaporized liquid is entrained in the pressurized gas. The pressurized gas is then discharged from the humidifier outlet and is provided to the patient via a patient hose as disclosed in U.S. Pat. No. 7,195,014.

The humidifier assembly further includes an electrically powered heating element that is disposed in contacting relationship with a tray suspended within the reservoir. The heating element is specifically adapted to heat the tray and vaporize the liquid which thereafter becomes entrained within the flow of pressurized gas discharged from the blower device. The humidifier assembly may further include a control base which is adapted to support the reservoir thereon. The housing assembly containing the silencer and motor blower unit is supported on the control base of the humidifier assembly.

BRIEF DESCRIPTION OF THE DRAWINGS

These and other features of the present invention will become more apparent on reference to the drawings wherein:

FIG. 1 is a perspective view of the blower device comprising a motor blower unit and a silencer housed within a housing assembly;

FIG. 2 is an exploded perspective view of the blower device of FIG. 1 illustrating the operational components including the power source, the housing assembly containing the silencer, and a humidifier assembly for the blower device;

FIG. 3 is an exploded perspective view looking downwardly on the housing assembly comprising an outer cover, an intermediate frame and a lower frame which collectively house the silencer and the motor blower unit;

FIG. 4 is an exploded perspective view looking upwardly at the housing assembly and illustrating an inlet formed in the lower frame and further illustrating the inlet being fluidly connected to an acoustic housing;

FIG. 8 is an exploded perspective view of the acoustic housing and illustrating a combination of reactive components, resonators and dissipative elements disposed therewithin and configured to attenuate various frequency bands;

FIG. 9 is a perspective view of the acoustic housing illustrating an inlet chamber and an acoustic chamber formed therein;

DETAILED DESCRIPTION

Figure 5:
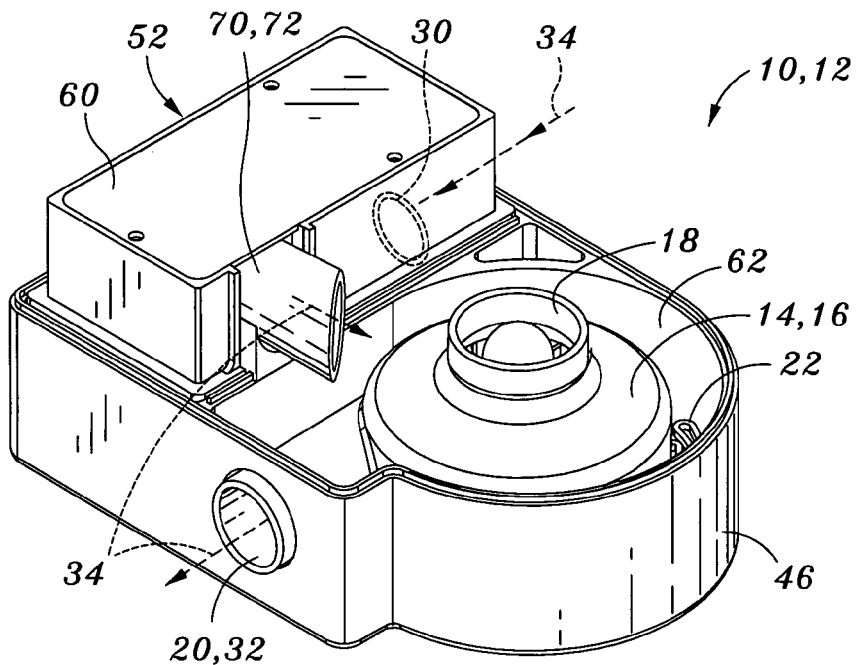
FIG. 5 is a perspective view of the lower frame illustrating the mounting of the acoustic housing and the motor blower unit.

Referring now to the drawings wherein the showings are for purposes of illustrating preferred embodiments of the present invention and not for purposes of limiting the same, shown is a passive silencer 10 adapted for use with a blower device 12. In one embodiment, the blower device 12 is configured as a continuous positive airway pressure (CPAP) device although the passive silencer 10 may be used in a variety of other ventilation systems. Exemplary uses of the passive silencer 10 include a bedside or tabletop-mounted blower device as disclosed in commonly-owned U.S. Pat. No. 7,195,014 entitled "Portable Continuous Positive Airway Pressure System", the entire contents of which is incorporated by reference herein. However, the passive silencer 10 may also be used in portable or wearable versions of the CPAP device.

The passive silencer 10 may be implemented in several embodiments of which two are illustrated in FIGS. 1-23. More specifically, FIGS. 1-14 illustrate the integration of the passive silencer 10 into a housing assembly 28 containing a variety of noise attenuation mechanisms and which further houses a motor blower unit 14. As can be seen in FIGS. 1 and 2, a power source 24 for the blower device 12 may be mounted to one side thereof such as using a pair of mounting clips 26. The housing assembly 28 is optionally mountable on a humidifier assembly 100 for humidifying the pressurized gas that is generated by the blower device 12.

The configuration of the silencer 10 illustrated in FIGS. 1-14 includes a combination of reactive components 70, resonators 80 and dissipative elements 92 which are each configured to attenuate a broad range of frequencies generated by air entering and passing through the motor blower unit 14. Likewise, the configuration of the passive silencer 10 illustrated in FIGS. 15-23 incorporates a combination of the above-mentioned acoustic attenuation mechanisms of the reactive components 70, resonators 80 and dissipative elements 92. The arrangement of the housing assembly 28 illustrated in FIGS. 1-14 is such that the footprint or size (i.e., cross sectional area) occupied by the housing assembly 28 is slightly smaller than that which is occupied by the housing assembly 28 illustrated in FIGS. 15-23.

Although the total volume occupied by the configuration of FIGS. 1-14 is similar to the total volume occupied by the configuration of FIGS. 15-23, each of the housing assemblies 28 define a different flow path 34. For example, the flow path 34 defined by the housing assembly 28 of FIGS. 1-14 includes two right-angle turns whereas the flow path 34 defined by the housing assembly 28 of FIGS. 15-23 includes a single right-angle turn. Furthermore, the flow path 34 for the housing assembly 28 of FIGS. 15-23 defines a substantially horizontal plane whereas the flow path 34 defined by the housing assembly 28 of FIGS. 1-14 is horizontal and vertical. However, it should be noted that the housing assembly 28 may be configured such that the flow path 34 defines any number of turns each of any angular dimension (e.g., sixty degrees, ninety-degrees, one-hundred-eighty degrees, etc.) and any combination of vertical and horizontal turns.

Regardless of the configuration of the housing assembly 28, the silencer 10 incorporated thereinto is specifically adapted to reduce the level of noise transmitted to ambient. Advantageously, the passive silencer 10 as disclosed herein complements the noise attenuation features incorporated into the blower motor unit disclosed in U.S. Pat. No. 7,195,014 to provide a blower device 12 that is useable in noise-sensitive environments. For example, the blower devices 12 illustrated in FIGS. 1-23 meets the above-mentioned EPA-recommended maximum noise levels for hospital of 45 decibels (dB) during the day and 35 dB at night. Moreover, due to the various combinations of noise attenuation features, the passive silencer 10 in at least one embodiment disclosed herein and illustrated in FIGS. 15-23 reduces noise output to as low as 25 dB.

Referring particularly now to FIGS. 1-2, shown is the blower device 12 having the silencer 10 incorporated therein. In its broadest sense, the silencer 10 comprises the housing assembly 28 which includes at least one of an inlet chamber 48, an acoustic chamber 50 and a blower chamber 62. Each one of the chambers is enclosed and defined by chamber walls 64 on peripheral, upper and lower sides of the respective chambers. Each of the chambers includes an inlet 30 and an outlet 32. As was earlier mentioned, the silencer 10 is disposed on a blower inlet 18 side of the motor blower unit 14. In this regard, the silencer 10 is specifically adapted for attenuating noise generated by air passing into and through the motor blower unit 14. Such air movement noise is generally broadband in nature and is attenuated by the combination of reactive components 70, resonators 80, and dissipative elements 92 that make up the silencer 10. However, the silencer 10 is also effective in attenuating mechanical noise generated by operation of the motor assembly which is typically narrowband or single-frequency in nature and is understood to fall within the broad frequency bandwidth of air movement noise which is attenuated by the silencer 10.

Figure 14:
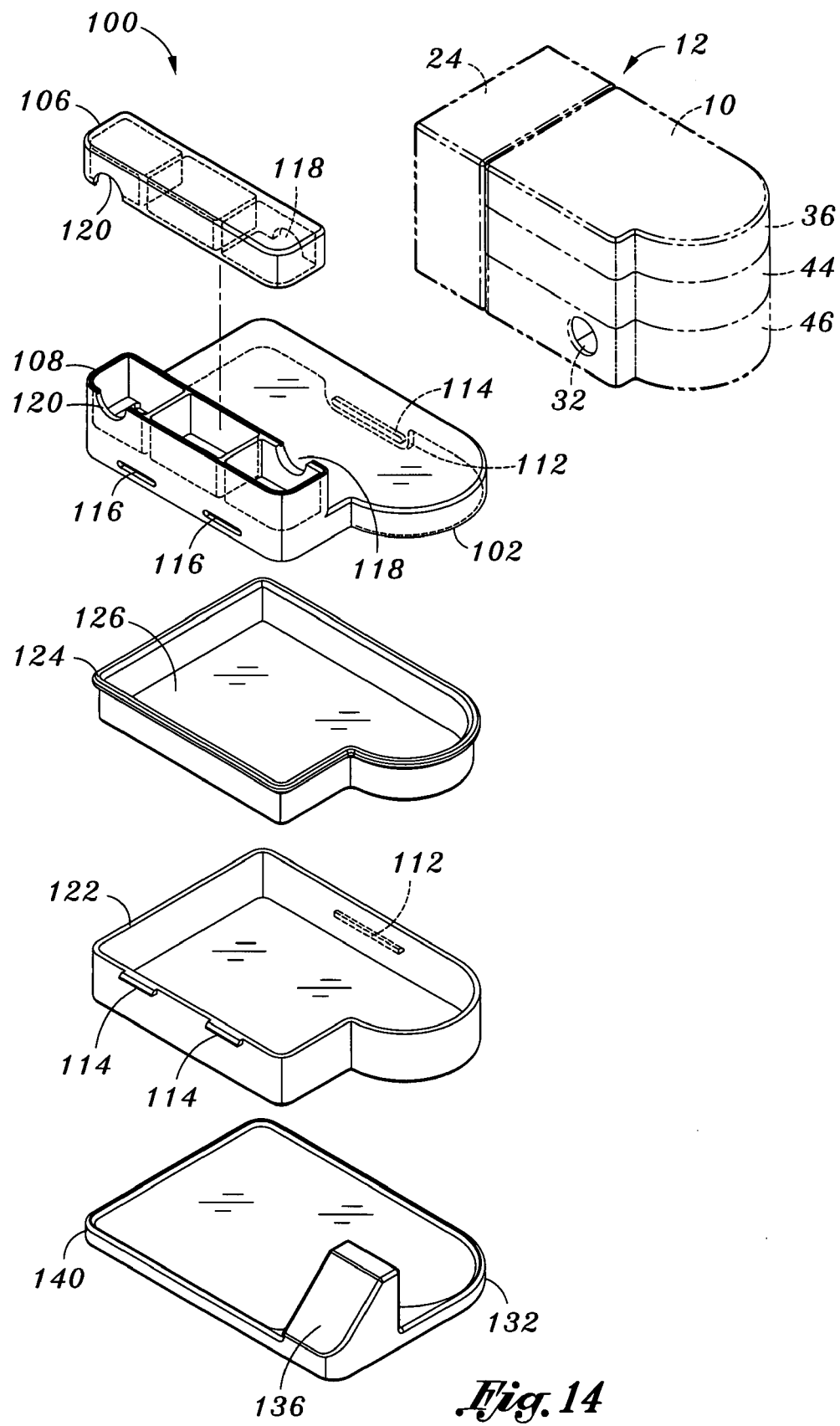
FIG. 14 is an exploded perspective view of the humidifier assembly shown in FIGS. 1 and 2 and illustrating a cover assembly, a container and a control base which make up the humidifier assembly.
Figure 15:
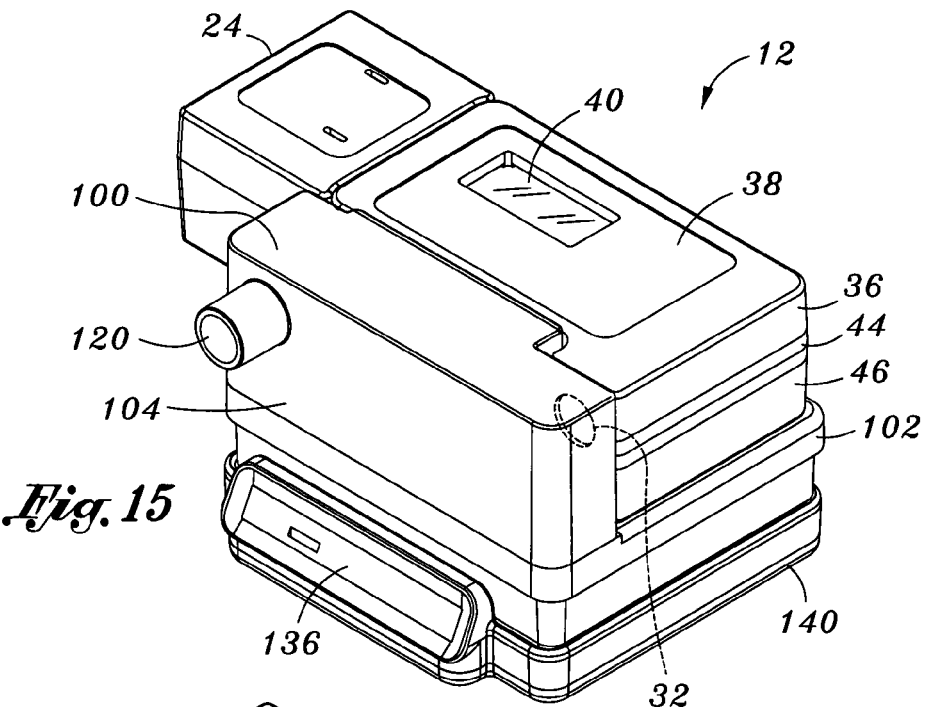
FIG. 15 is a perspective view of the blower device illustrating the housing assembly configured in an alternative embodiment.
Figure 16:
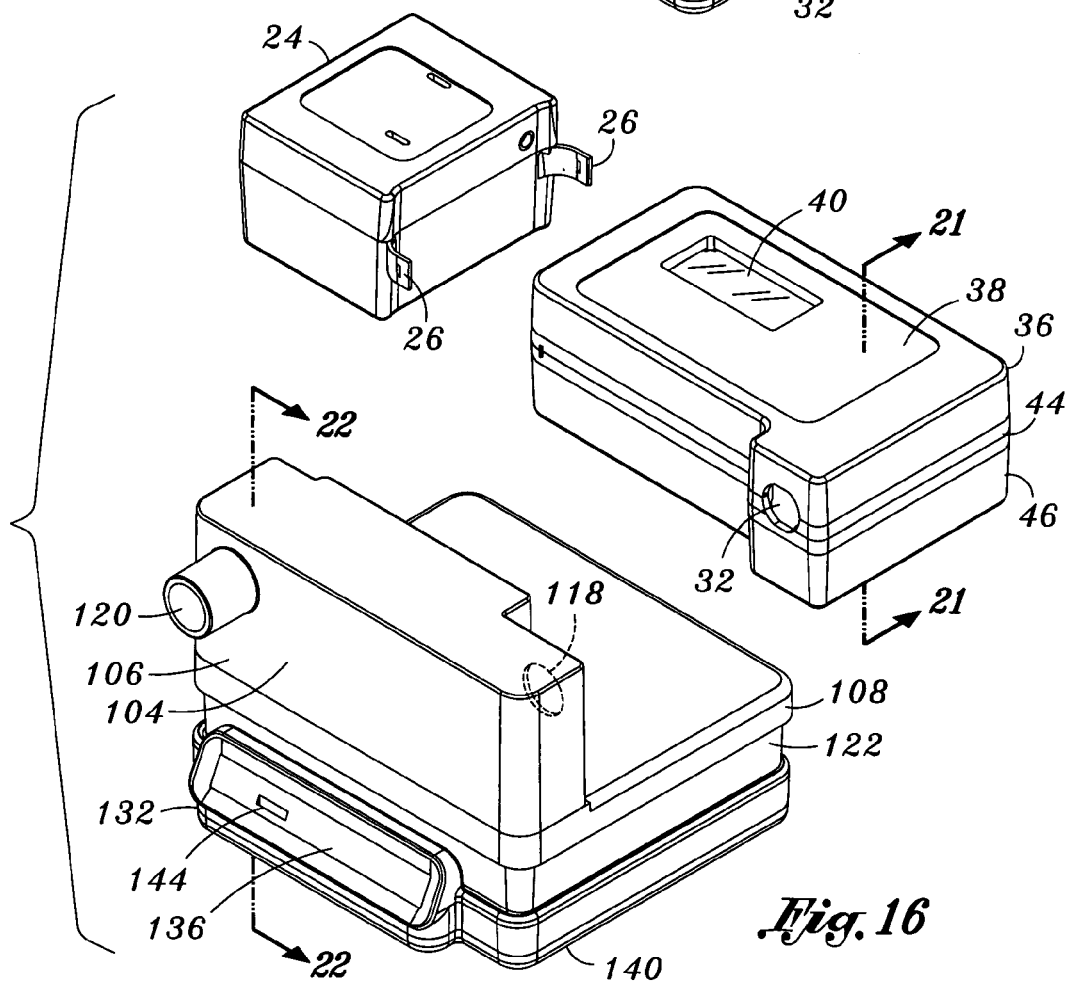
FIG. 16 is an exploded perspective view of blower device of FIG. 15 and illustrating the power source, housing assembly and humidifier assembly that make up the blower device.
Figure 23:
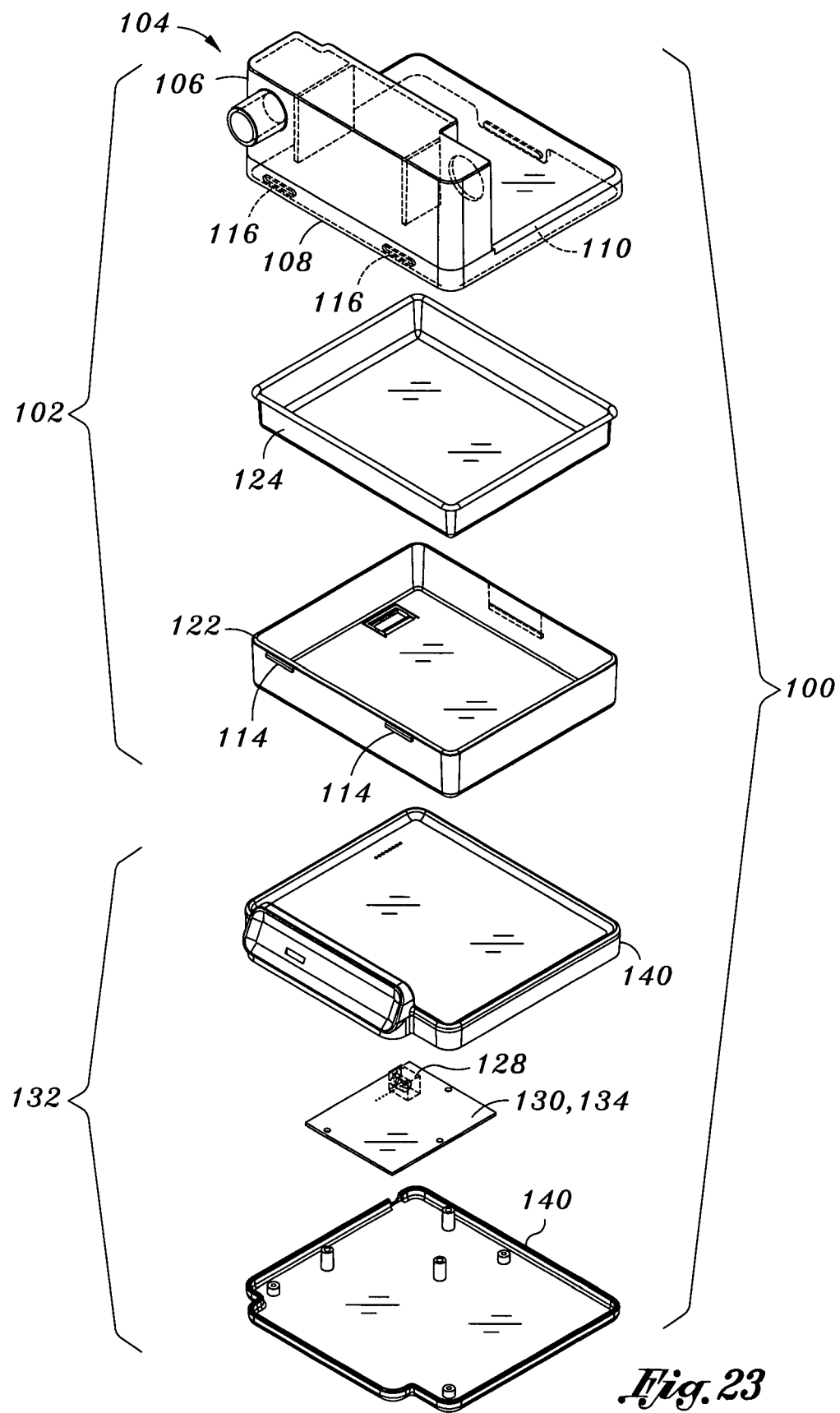
FIG. 23 is an exploded perspective view of the humidifier assembly in the embodiment illustrated in FIGS. 15 and 16.

Referring still to FIGS. 1 and 2, shown is the blower device 12 comprising the housing assembly 28 containing the silencer 10 and the motor blower unit 14. Optionally secured to the housing assembly 28 is a self-contained power source 24 such as a battery pack to provide power to the blower device 12. The blower device 12 may optionally include a humidifier assembly 100 which is placed in fluid communication with the housing assembly 28 such that compressed air produced by the motor blower unit 14 enters the humidifier assembly 100. Vaporized liquid produced by the humidifier assembly 100 becomes entrained within the pressurized gas flow and is discharged from the humidifier assembly 100 for delivery to the patient. The structure and function of the humidifier assembly 100 illustrated in FIGS. 14 and 23 is described in greater detail below.

The power source 24 shown in FIGS. 1 and 2 may be configured as a rechargeable battery pack which is electrically connectable to the blower device 12 such as by an electrical jack. The battery pack is configured to be compact and removably attachable to the housing assembly 28 in the manner illustrated in FIG. 2. Preferably, the battery pack incorporates a highly-efficient battery such as a lithium ion battery in order to maximize operating time between recharges or battery replacement. In this regard, the battery pack may be fitted with a charging receptacle or jack to allow recharging of the battery pack. Advantageously, the high efficiency of the motor blower unit 14 allows operation of the CPAP device for extended periods of time. Optionally, the power source 24 may be configured with an A.C. adaptor to allow powering of the blower device 12 by connection to an A.C. power source available at a common wall outlet.

Figure 13:
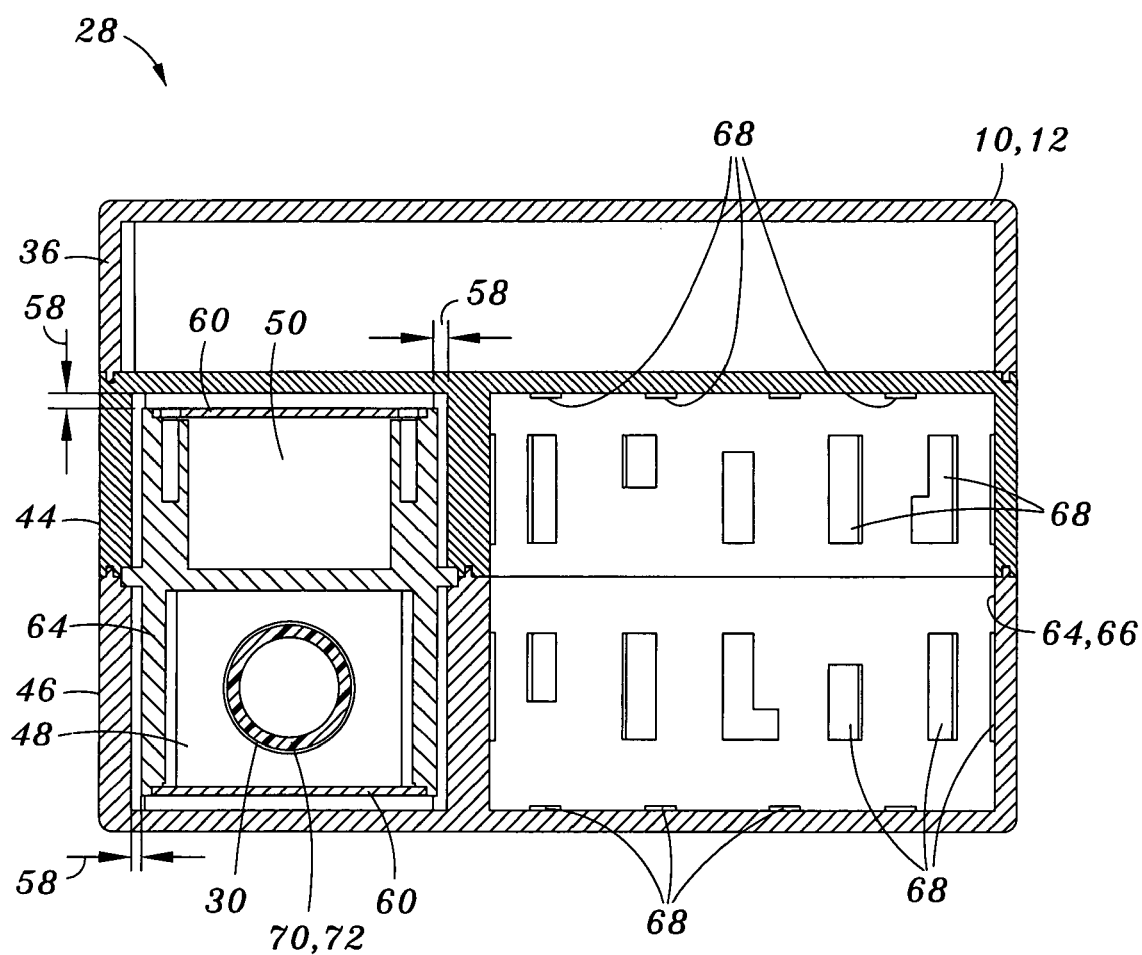
FIG. 13 is a cross sectional view of the housing assembly illustrating the outer cover, intermediate frame and lower frame in the assembled state and further illustrating the mounting of the acoustic housing within a cavity volume collectively defined by the lower and intermediate frames.

FIGS. 3 and 4 perspectively illustrate the housing assembly 28 which comprises the outer cover 36, intermediate frame 44 and lower frame 46 and which collectively define the inlet chamber 48, acoustic chamber 50 and blower chamber 62. As can be seen, the motor blower unit 14 is configured to be installed in the blower chamber 62 with a blower outlet 20 being aligned with an outlet 32 formed in the lower frame 46. The outer cover 36 may be formed as an integrally-molded unitary structure and may include a blower control panel 38 and a display 40 for regulating operation of the blower device 12. An electronics control panel (not shown) operatively connected to the blower control panel 38 and display 40 may be located within the hollow confines of the outer cover 36 as best seen in FIG. 13. The outer cover 36 is configured to be mated to the intermediate frame 44 and may include mechanical features such as a ridge extending along a perimeter and which is sized and configured to engage a corresponding groove formed in the intermediate frame 44.

As best seen in FIGS. 3-4, the intermediate frame 44 and lower frame 46 collectively define the inlet chamber 48, acoustic chamber 50 and blower chamber 62. The intermediate frame 44 is constructed similar to that described above for the outer cover 36 in that the intermediate frame 44 may be formed as a unitary structure such as by injection molding of polymeric material. The interior surfaces 66 of the relatively long and/or wide chamber walls 64 preferably include randomly-placed, locally thick sections 68 configured to minimize the generation of a single low frequency resonant response of the single panel (i.e., chamber wall).

The randomly-placed thick sections 68 are configured to induce the generation of a plurality of different high frequency resonances each of which has a much lower amplitude in comparison to the relative higher-amplitude lower frequency resonant response of a single panel. As can be seen in FIG. 3, the interior surfaces 66 of the chamber walls 64 of the lower frame 46 may additionally include randomly-placed and irregularly-shaped thick sections 68. For example, the randomly-placed thick sections 68 may also be disposed on the peripheral chamber walls 64 as well as on the lower chamber walls 64 of the blower chamber 62.

Figure 6:
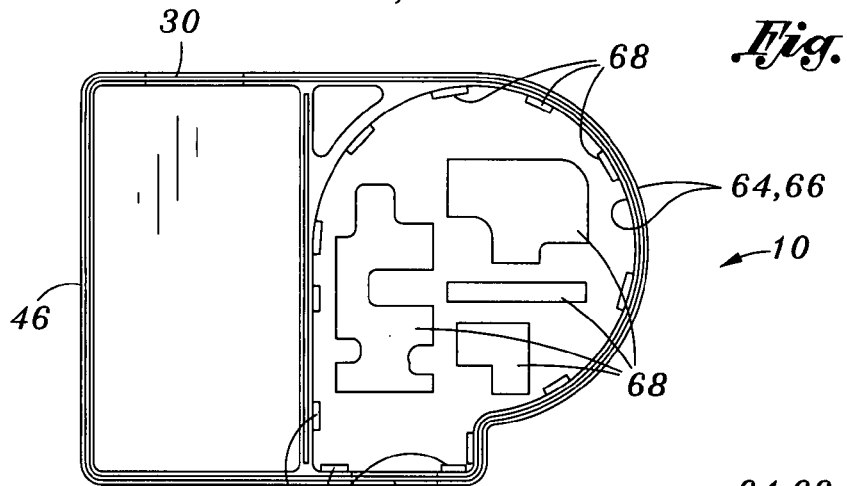
FIG. 6 is a plan view of the lower frame illustrating the blower chamber having a plurality of thick sections formed on a chamber wall of the blower chamber.
Figure 7:
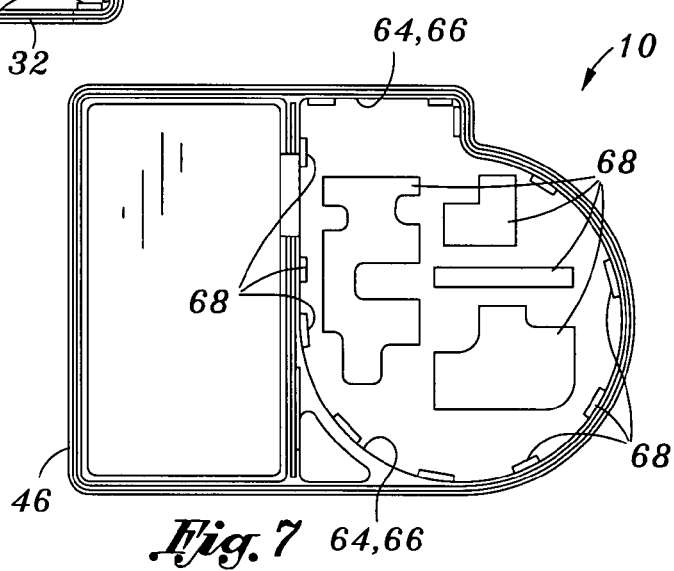
FIG. 7 is a plan view of an interior side of the intermediate frame.

Referring to the intermediate frame 44 illustrated in FIG. 6, the upper and peripheral chamber walls 64 of the blower chamber 62 portion of the intermediate frame 44 may likewise include a plurality of the thick sections 68 each sized and configured (i.e., shaped) to generate a differing high frequency response. Likewise, as best seen in FIG. 7, the lower chamber wall 64 and peripheral chamber walls 64 defining the blower chamber 62 in the lower frame 46 include a plurality of the thick sections 68. The attenuation of vibration in the chamber walls 64 prevents or minimizes the outward radiation of such vibrations as sound. As will be described in detail below, sound output of the blower device 12 is reduced by the combination of reactive components 70, resonators 80 and dissipative elements 92 which are each preferably configured to attenuate differing but preferably overlapping frequency bands.

Referring more particularly now to FIGS. 3-5 and 13, shown is an acoustic housing 52 which is specifically adapted to be separately mountable within the housing assembly 28. In addition, the acoustic housing 52 is adapted to be mounted in spaced relation to the housing assembly 28 such that the acoustic housing 52 and the housing assembly 28 collectively define a housing gap 58 therebetween. As best seen in FIG. 13, the housing gap 58 preferably exists along a majority of the exterior surfaces of the acoustic housing 52 and the interior surfaces 66 of the housing assembly 28. By mounting the acoustic housing 52 within the housing assembly 28 as shown in FIGS. 3-5 and 13, the acoustic housing 52 is essentially a free-standing enclosure beyond which transmission of structure-borne vibration is largely attenuated.

As was earlier mentioned, structure-borne vibration transmitted into the device housing can be radiated outwardly from the blower device 12 as sound. For applications wherein the silencer 10 is incorporated into a wearable CPAP device or where the CPAP devices operates in close proximity to the patient, such vibration can be a source of discomfort and annoyance. However, by mounting the acoustic housing 52 in such a manner as to provide the housing gap 58 between the acoustic housing 52 and the housing assembly 28, the transmission of structure-borne vibration to the housing assembly 28 is minimized.

As best seen in FIG. 13, the acoustic housing 52 includes a ridge extending around a periphery at an approximate mid-height of the acoustic housing 52. The intermediate frame 44 and lower frame 46 collectively define a complimentary groove that is sized and configured to receivably engage the ridge 114 extending around the perimeter of the acoustic housing 52. FIG. 13 further illustrates the housing gap 58 extending between upper and lower acoustic covers 60 which enclose the acoustic housing 52. Although shown as being mechanically securable to the vertical walls of the acoustic housing 52 by means of screws threadably engaged thereto, each of the upper and lower acoustic covers 60 may optionally be integrally formed with the acoustic housing 52 or may be separately formed and secured to the acoustic housing 52 by means of non-mechanical means including sonic welding, chemical bonding and the like.

Referring to FIGS. 8 and 9, shown are upper and lower acoustic covers 60 each optionally including a plurality of the above-mentioned randomly-placed thick sections 68 configured to induce the acoustic covers 60 to generate multiple differing high frequency resonances instead of a single low frequency resonant response. Although a plurality of thick sections 68 are shown on each of the chamber walls 64, a single thick section 68 may also be applied thereto. Furthermore, it should be noted that although the thick sections 68 are shown as being applied to interior surfaces 66 of the chamber walls 64, the thick sections 68 may be formed on exterior surfaces or on a combination of interior and exterior surfaces of any of the chamber walls 64 throughout the housing assembly 28. However, for aesthetic, manufacturing and assembly purposes, the thick sections 68 are preferably located on interior surfaces 66.

Referring to FIGS. 8-12, the separately-mounted acoustic housing 52 includes the inlet chamber 48 and an acoustic chamber 50 which itself is comprised of a first chamber 54 and a second chamber 56. As best seen in FIG. 9, the inlet chamber 48 is located on a lower end of the acoustic housing 52 and includes an inlet 30 and an outlet 32 on opposed ends of the inlet chamber 48. The inlet chamber 48 includes a reactive component configured as a reactive tube 72 extending through the inlet chamber 48 and passing through the inlet 30 and outlet 32. The reactive tube 72 preferably has a compliant wall defining a wall thickness 74. A cavity volume 82 is collectively defined by the reactive tube 72 and the chamber walls 64 of the inlet chamber 48. The reactive tube 72 further forms a resonator 80 within the inlet chamber 48 by which acoustic energy is attenuated.

Figure 11:
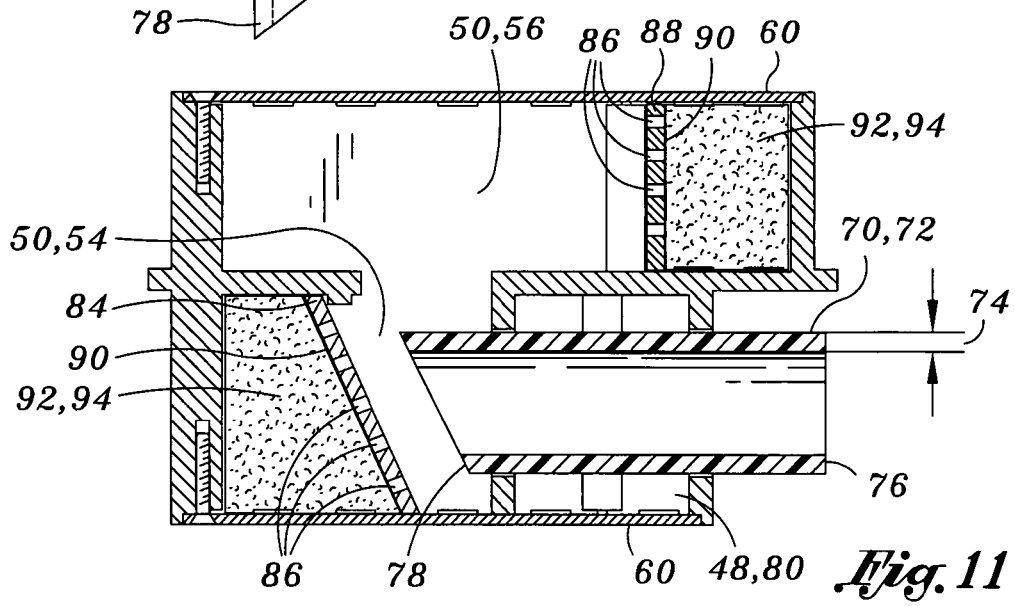
FIG. 11 is a cross sectional view of the acoustic housing taken along lines 11-11 of FIG. 10 and illustrating the reactive tube extending through the inlet chamber and further illustrating the positioning of the perforated plates within first and second chambers of the acoustic chamber.
Figure 12:
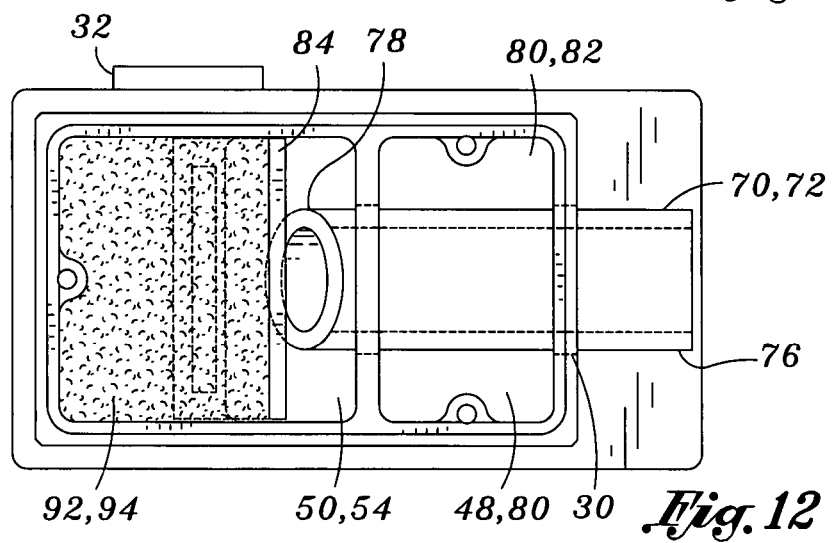
FIG. 12 is a bottom view of the inlet chamber and first chamber and illustrating the placement of the perforated plate backed by a dissipative element (i.e., foam) within the first chamber.

As best seen in FIG. 11, the reactive tube 72 includes a leading end 76 disposed adjacent the inlet 30 and a trailing end 78 disposed adjacent the outlet 32 of the inlet chamber 48. The leading end 76 of the reactive tube 72 preferably extends to the inlet 30 of the acoustic housing 52 as best seen in FIG. 4. Likewise, the trailing end 78 of the reactive tube 72 preferably extends past the outlet 32 of the inlet chamber 48 and is preferably formed at an angle in order to widen the attenuation band. Although shown at an angle of approximately 45 degrees, the trailing end 78 may be angled at any orientation to alter the attenuation bandwidth.

The inlet 30 and outlet 32 to the inlet chamber 48 are preferably sized and configured complimentary to the reactive tube 72. More specifically, the inlet 30 and outlet 32 are preferably sized and configured to provide a press-fit of the reactive tube 72 therewithin in order to stabilize the reactive tube 72 against movement during operation of the blower device 12. The interior surface of the reactive tube 72 is preferably smooth in order to minimize resistance to air and reduce the generation of noise as a result of air passing therethrough. The cross sectional area of the reactive tube 72 is preferably sized such that the flow velocity is maintained at less than approximately Mach 0.1. In this manner, the noise attenuation characteristics provided by the reactive component (e.g., compliant wall of the reactive tube) and resonator 80 (e.g., cavity volume 82 of the inlet chamber 48) allows maximum attenuation.

Referring still to FIGS. 8-12, the acoustic chamber 50 is comprised of a first chamber 54 and a second chamber 56. The first chamber 54 is illustrated as being generally aligned with the inlet chamber 48 and is fluidly connected thereto by means of the reactive tube 72. The second chamber 56 is disposed above the first chamber 54 and is partially separated therefrom by means of a horizontal ledge. As can be seen in FIG. 11, the first chamber 54 includes a perforated plate 84 disposed in angular orientation to the flow path 34 defined by the reactive tube 72. The perforated plate 84 may include a plurality of apertures 86 which are specifically sized and configured to provide attenuation of a specific frequency band. The attenuation characteristics are partially related to the total circumferential surface area of the apertures 86 extending through a plate thickness of the perforated plate 84.

In this regard, each one of the perforated plates 84 can, to a certain extent, be tuned to attenuate a desired frequency band as a function of the spacing and diameter of the apertures 86 formed in each perforated plate 84. For purposes of design and analysis, each of the perforated plates 84 provided in the housing assembly 28 are preferably of a uniform thickness, material (e.g., polycarbonate), and stiffness while the sizing and/or spacing of the apertures 86 is varied from plate-to-plate such that each of the perforated plates attenuates a different frequency band. The housing assembly 28 may include a single perforated plate 84 resonator 80 or a plurality of perforated plate 84 resonators 80.

Referring still to FIG. 11, the perforated plate 84 is disposed in angled relationship to the flow path 34 passing through the reactive tube 72. The perforated plate 84 has a front face 88 and a back face 90 with at least one dissipative element 92 comprising porous material 94 disposed therebehind and substantially occupying the cavity volume 82 collectively defined by the perforated plate 84 and the chamber walls 64. The second chamber 56 is disposed above the first chamber 54 and is separated therefrom by a longitudinal ledge formed integrally with the acoustic housing 52. The second chamber 56 includes a second reactive tube 72 extending into the blower chamber 62 as best seen in FIGS. 3, 5 and 8. In this regard, the second chamber 56 has a pair of reactive components 70 consisting of the second reactive tube 72 and the cavity volume 82 defined partially by the second reactive tube 72. The reactive tube 72 is preferably a compliant-walled reactive tube 72 to allow the cavity volume 82 extending around the reactive tube 72 to act as a resonator 80.

Figure 10:
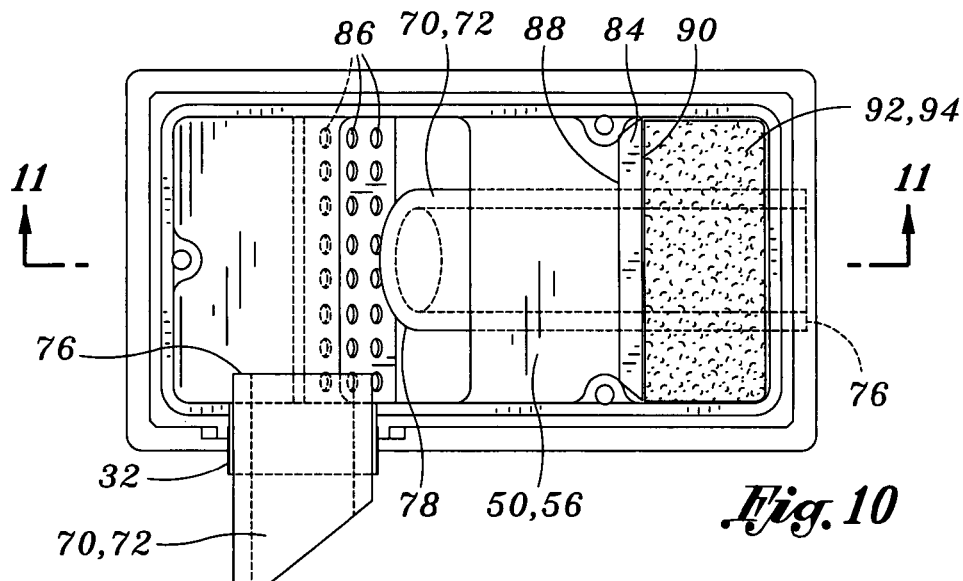
FIG. 10 is a top view of the acoustic chamber shown in FIGS. 8 and 9 and illustrating a pair of reactive tubes installed in respective ones of the inlet chamber and acoustic chamber and further illustrating a pair of perforated plates mounted within the acoustic chamber.

Referring to FIG. 8, the reactive tube 72 extending through the inlet chamber 48 is preferably of a different length than the second reactive tube 72 extending into the blower chamber 62. The reactive tubes 72 are preferably provided in different lengths to allow selective tuning to a different center frequency and attenuation of acoustic energy within different frequency bands. As best seen in FIG. 10, the trailing end 78 of the second reactive tube 72 is preferably angled or beveled similar to the beveled trailing end 78 of the first reactive tube 72 extending through the inlet chamber 48. As was earlier mentioned, orienting the trailing end 78 of each one of the reactive tubes 72 at an angle widens the attenuation band. The inner surface of the second reactive tube 72 has a smooth and uniform cross section. The inside diameter is sized and configured such that flow velocity does not exceed Mach 0.1 to prevent the flow from adversely affecting attenuation capability.

Referring to FIGS. 8 and 11, the second chamber 56 further defines a cavity volume 82 extending partially around the second reactive tube 72 in order to provide a resonator 80. Additionally, the second chamber 56 may further include a perforated plate 84 defining a cavity volume 82 and having porous material 94 substantially filling the cavity volume 82 in order to provide a dissipative element 92 for absorbing acoustic energy. Referring to FIG. 8, the dissipative elements 92 are configured as porous material 94 disposed in abutting contact with the back face 90 of the perforated plates 84. The porous material 94 element is preferably sized and configured to substantially occupy the cavity volume 82 bounded by the perforated plate 84 and the chamber walls 64 within which the perforated plate 84 is installed. Ideally, the porous material 94 is preferably an open-cell foam material having acoustic energy-absorbing capability. In order to achieve a different response in attenuation frequency bandwidth, it is contemplated that the foam may be provided in different compressabilities or softnesses providing different energy-absorbing responses.

Referring briefly to FIGS. 5 and 8, the reactive tubes 72 of the inlet chamber 48 and the outlet 32 of the acoustic chamber 50 are preferably oriented out of line-of-sight with one another in order to provide an additional noise attenuation feature. In this regard, the configuration of the housing assembly 28 preferably provides a relatively complex flow path 34 for air movement through the silencer 10. For the arrangement of the housing assembly 28 illustrated in FIGS. 1-14, the flow path 34 between the inlet chamber 48 and the blower chamber 62 includes at least two right-angle turns. Each right-angle turn preferably defines a turning plane such that the right-angle turns are oriented in non-planar relationship to one another.

More specifically, referring to FIG. 11, the flow path 34 from the inlet 30 of the inlet chamber 48 passes into the first chamber 54. The perforated plate 84 is oriented at an angled relationship to the reactive tube 72 such that the acoustic energy in the flow path 34 produces a grazing flow against the perforated plate 84 which increases resonator 80 losses. The flow path 34 reflects against the perforated plate 84 and moves upwardly into the second chamber 56 to define the first right-angle turn. The flow path 34 then defines a second right-angle turn wherein the flow path 34 passes through the second reactive tube 72 and enters the blower chamber 62 as best seen in FIG. 11. The change in direction and lack of line-of-sight of the flow path 34 to the inlet 30 of the inlet chamber 48 enhances the attenuation characteristics of the silencer 10.

Referring briefly to FIGS. 15-23, the flow path 34 between the inlet chamber 48 and the blower chamber 62 of the housing assembly 28 includes a single ninety-degree turn which prevents line-of-sight of the flow path 34 from the blower outlet 20 to the source (i.e., the inlet 30 of the housing assembly 28) and further provides a broadband attenuation affect. In this regard, the housing assembly 28 illustrated in FIGS. 15-23 generally orients the attenuation features (i.e., reactive components 70, resonators 80 and dissipative elements 92) in a horizontal plane as opposed to the generally vertical arrange arrangement of the housing assembly 28 illustrated in FIGS. 1-14.

Referring briefly to FIGS. 3-5, shown is the motor blower unit 14 which is installable within the blower chamber 62 disposed adjacent the acoustic housing 52. In one embodiment, the motor blower unit 14 is similar to that which is disclosed and illustrated in U.S. Pat. No. 7,012,346 wherein the motor blower unit 14 comprises a blower housing 16. The blower housing 16 includes an annular blower inlet 18 and having a centrifugal impeller powered by a brushless D.C. motor assembly. The impeller is configured to compress air drawn into the annular blower inlet 18 and discharge the compressed air from the blower outlet 20 as illustrated in FIG. 3. The motor blower unit 14 is mounted within the blower chamber 62 such that the blower outlet 20 is aligned with the outlet 32 of the housing assembly 28.

As can be seen in FIGS. 3-5, the blower housing 16 may optionally include a plurality of suspension mounts 22 extending laterally outwardly from the blower housing 16. Each of the suspension mounts 22 is preferably sized and configured to support the blower housing 16 within the blower chamber 62 and, more preferably, is configured to attenuate vibration (e.g., radial and axial vibration) generated during operation of the motor blower unit 14. The suspension mounts 22 may be specifically tailored to attenuate vibration in accordance with the mass and operating characteristics of the motor blower unit 14. In this regard, the suspension mounts 22 may attenuate vibration within a specific frequency range.

As best seen in FIG. 5, each of the suspension mounts 22 may be configured as a serpentine spring member having a free end which is configured to be engageable to or mounted within the lower frame 46 of the housing assembly 28. The suspension mounts 22 are adapted to prevent transmission of vibration from the motor blower unit 14 to the housing assembly 28 of the CPAP device. In this regard, it is contemplated that the acoustic housing 52 illustrated in FIG. 8 may be mounted to the housing assembly 28 using a similar system of suspension mounts 22. In such an arrangement, the acoustic housing 52 is preferably suspended within the housing assembly 28 such that the housing gap 58 is maintained as illustrated in FIG. 13.

Referring particularly now to FIG. 14, shown is a humidifier assembly 100 specifically configured for use with the blower device 12 described above and illustrated in FIGS. 1-13. Broadly, the humidifier assembly 100 comprises a reservoir 102 which includes a container 122 and a cover assembly 104 engageable to the container 122. The reservoir 102 is adapted for containing a liquid such as water to be vaporized. The vaporized liquid is entrained into the flow of pressurized gas entering the humidifier assembly 100 from the blower device 12. The pressurized gas flow is discharged from the outlet 32 as best seen in FIG. 2 and enters the humidifier inlet 118 located on a back side of the cover assembly 104. Upon entering the humidifier inlet, the flow path 34 is directed downwardly into the reservoir 102. The liquid contained therewithin is vaporized by the heating element 126 and becomes entrained within the pressurized gas flow and is carried out of the humidifier outlet 120 located on a front side of the humidifier assembly 100 as shown in FIGS. 1 and 2.

The humidifier assembly 100 is illustrated in exploded view in FIG. 14 which shows the cover assembly 104 comprising a cover top portion 106 and a cover bottom portion 108 engageable to the cover top portion 106. Collectively, the cover top and bottom portions 106, 108 define the humidifier inlet 118 and humidifier outlet 120 which are separated form one another such as by a spaced pair of walls. The cover assembly 104 has a footprint which generally approximates the combined footprint of the housing assembly 28 and power source 24 mounted thereto. The cover assembly 104 is preferably fabricated of a transparent or translucent polymeric material suitable for injection molding. Likewise the container 122 which is engageable to the cover assembly 104 is also preferably fabricated of a transparent polymeric material such that the level of the fluid contained within the reservoir 102 is easily ascertainable without disassembling the humidifier assembly 100.

The cover assembly 104 may include a cover seal 110 for sealingly engaging the container 122 to thereby maximize vaporizing efficiency. Furthermore, the cover assembly 104 is preferably releasably engageable to the container 122 by means of tab 112 having a linear ridge 114 formed thereon. The tab 112 is disposed on the backside of the cover assembly 104. On a front side, the cover assembly 104 may include a pair of elongate slots 116 which are engageable to a mateable pair of ridges 114 as best seen in FIG. 14. The reservoir 102 preferably includes a tray 124 constructed of a heat conductive material such as stainless steel and which is suspended above the bottom panel of the container 122 by an outwardly turned lip extending along a perimeter edge of the tray 124.

Figure 22:
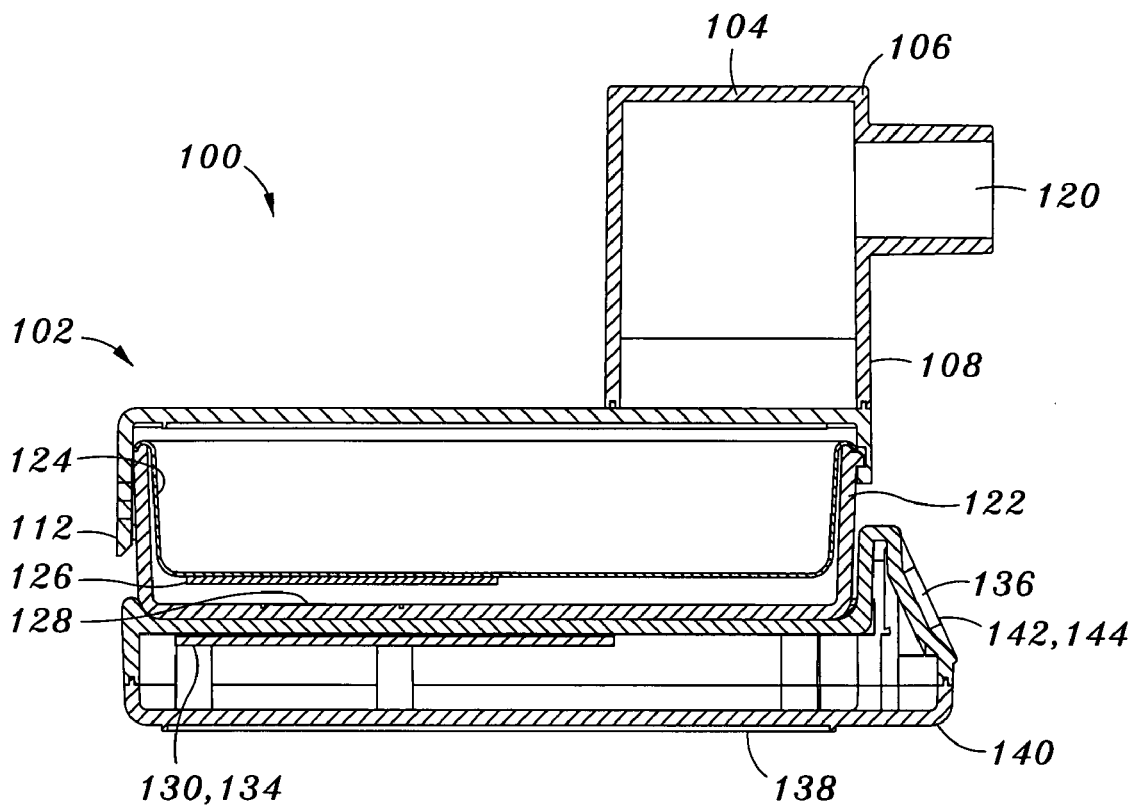
FIG. 22 is a cross sectional view of the humidifier assembly taken along lines 22-22 of FIG. 16 and illustrating the interconnectivity of the cover assembly with the container and control base.

The tray 124 may include an electrically-powered heating element 126 disposed in contacting relationship with an underside of the tray 124 as best seen in FIG. 22. The heating element 126 may be configured as a flex circuit having terminal pads mounted on the bottom panel of the container 122 and configured to be engageable to spring pins mounted on a top surface of the control base 132. As shown in the figures, the container 122 rests atop the control base 132. The control base 132 provides power to the heating element 126 and includes heat control circuitry 134 with temperature-sensing capability and on/off control of the heating element via electrical connectors 128. The control base 132 may further include a user interface such as a humidifier control panel 136 shown in the figures. The humidifier control panel 136 may be integrally formed with the control base 132 as part of a base housing 140. The base housing 140 is enclosed on its bottom side by a removable base plate 138 to allow access to the interior of the base housing 140 housing the heat control circuitry 134.

The user interface (i.e., humidifier control panel 136) may be provided with a plurality of switches in order to allow regulation of the humidifier assembly 100. More specifically, the humidifier control panel 136 may include three push button switches 142 including an on/off switch, and two temperature control switches including a temperature-up and a temperature-down switch. The humidifier control panel 136 may further include a plurality of light-emitting diodes 144 (LED's) to indicate one of several predetermined temperature settings.

The heat control circuitry 134 may be configured as a PIC microcontroller or other suitable mechanism wherein one of several predetermined temperature settings is selectable by activating the temperature-up or temperature-down switches. The microcontroller may be further configured to activate the heating element 126 when feedback from the temperature sensor in the reservoir 102 indicates that the temperature has fallen below a minimum threshold. Likewise, the microcontroller is preferably operative to activate the heating element 126 when the temperature sensing/control mechanism has risen above a maximum predetermined threshold. As a safety precaution, the heat control circuitry 134 may include a thermal switch 130 operative to deactivate the heating control element if the temperature sensing/control mechanism detects an open circuit or a short circuit.

Referring now to FIGS. 15-23, shown is the housing assembly 28 in an alternative embodiment wherein the flow path 34 through the silencer 10 is generally horizontal and preferably includes at least one ninety-degree turn as described above. As in the housing assembly 28 configuration of FIGS. 1-14, the inlet chamber 48 is preferably out of line-of-sight with the outlet 32 of the acoustic chamber 50 in order to minimize transmission of noise to ambient. In this regard, the configuration illustrated in FIGS. 15-23 shares many of the same attenuation features as that described above with reference to the housing assembly 28 of FIGS. 1-14.

Figure 19:
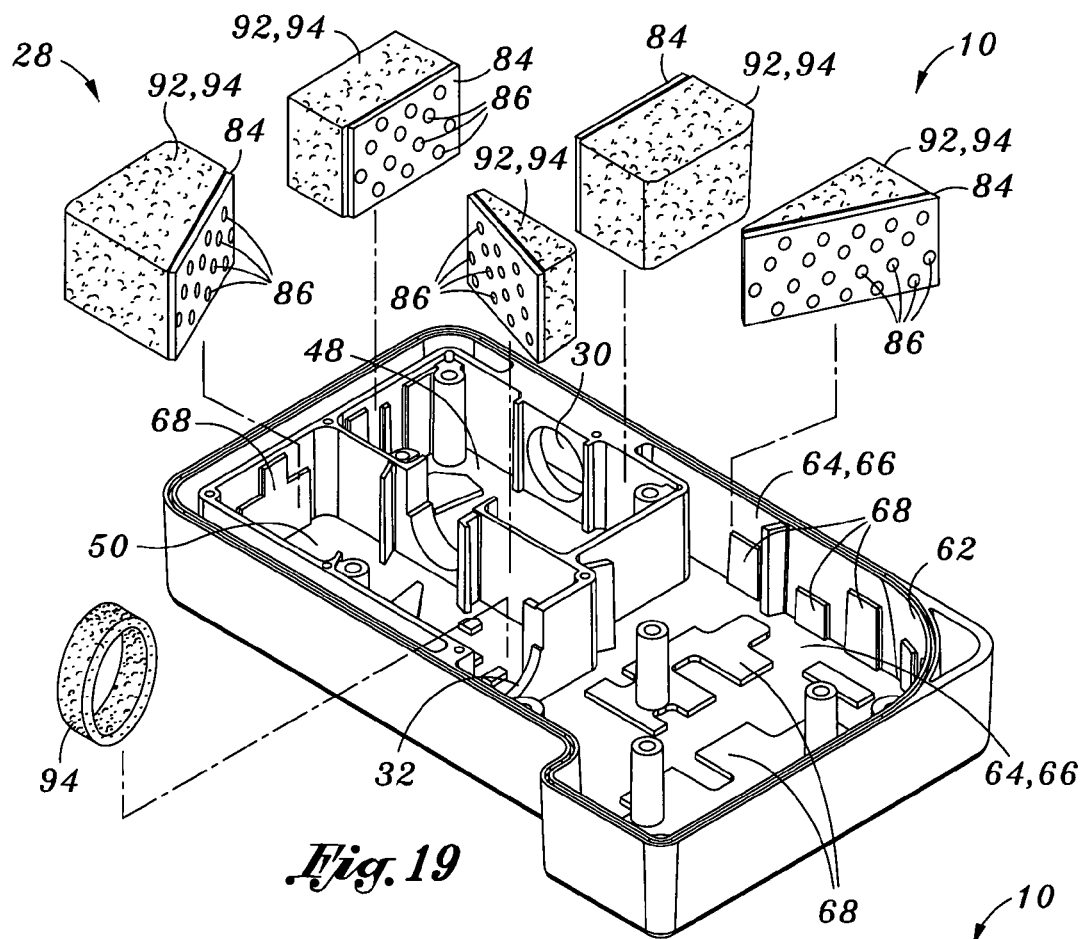
FIG. 19 is an exploded perspective view of the reactive components, resonators and dissipative elements that make up the silencer for the housing assembly embodiment illustrated in FIGS. 15 and 16.
Figure 20:
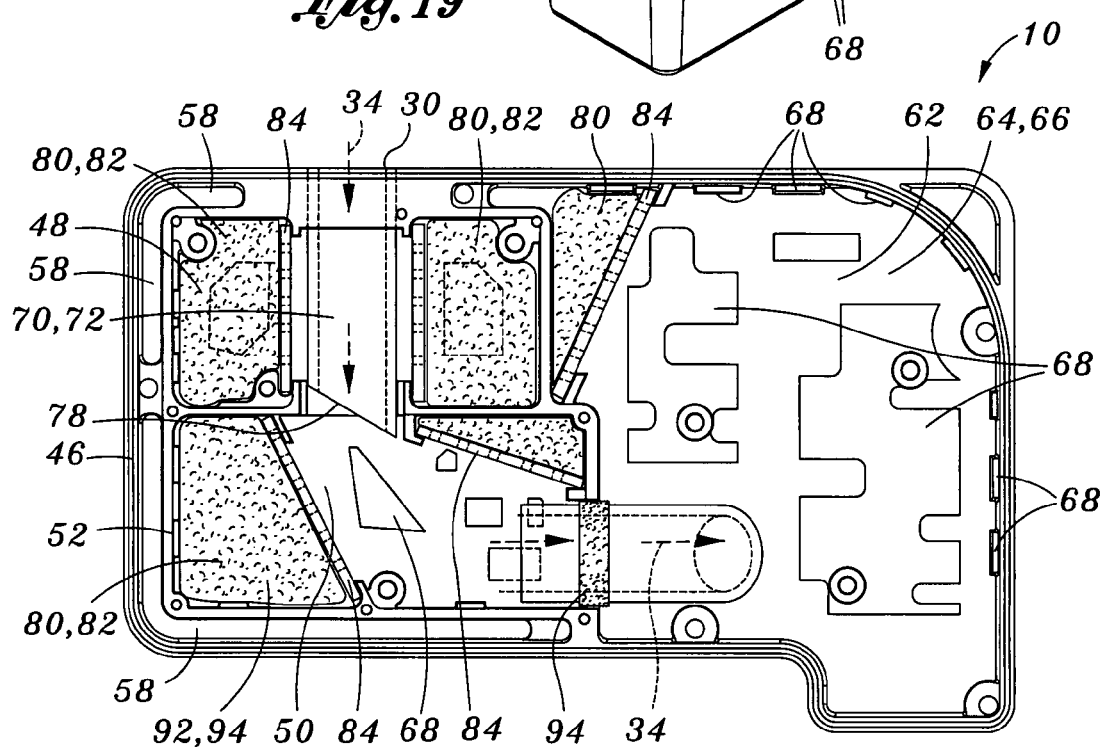
FIG. 20 is a plan view of the lower frame illustrating the installation of the reactive components, resonators and dissipative elements.

For example, each of the housing assemblies 28 includes at least one of the inlet chamber 48, acoustic chamber 50 and blower chamber 62 with each chamber being enclosed by chamber walls 64 and optionally having a plurality of locally thick sections 68 to prevent vibration of the chamber walls 64 at a single low frequency resonance. Instead, the locally thick sections 68 induce multiple higher frequency resonances. The housing assembly 28 illustrated in FIGS. 15-23 includes a combination of reactive components 70, resonators 80 and dissipative elements 92. As described above, the reactive components 70 may comprise a compliant-walled reactive tubing mounted in the inlet chamber 48 and in the outlet 32 of the acoustic chamber 50. However, as best seen in FIGS. 19 and 20, the reactive tube 72 extending through the inlet chamber 48 is preferably bounded on opposing longitudinal sides by a pair of perforated plates 84.

The perforated plates 84 are preferably disposed in spaced arrangement to the reactive tube 72 and are preferably backed by dissipative elements 92 comprised of porous material 94 such as open-cell foam which fills the cavity volume 82 bounded by the inlet chamber 48. The porous material 94 is preferably disposed in abutting contact with a back face 90 of the perforated plate 84 and functions as an energy absorber. Furthermore, the dissipative foam acts to lower the quality factor (Q) of the inlet chamber 48 by filling the cavity volume 82 which generally lowers the Q. A lower Q translates to an increase in dissipative capability and thereby broadens the attenuation frequency bandwidth.

Figures 17, 18:
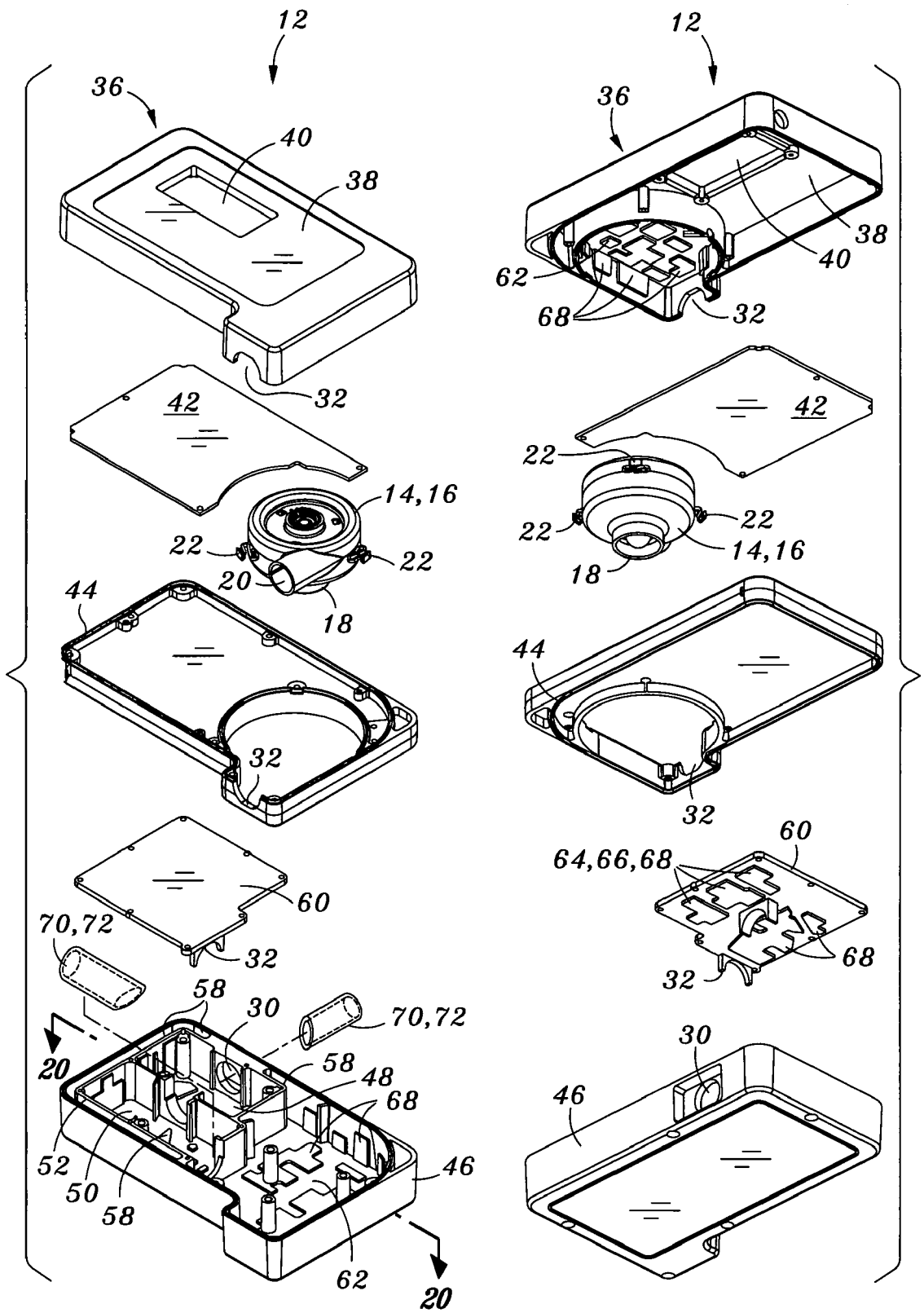
FIG. 17 is an exploded perspective view of the housing assembly in the embodiment shown in FIGS. 15 and 16 and illustrating the acoustic housing integrally formed with the lower frame.
FIG. 18 is a perspective view looking at an underside of the housing assembly and illustrating the plurality of thick sections formed on interior surfaces of the chamber walls of the acoustic chamber and the blower chamber.

Regarding the overall configuration of the housing assembly 28, FIGS. 17 and 18 illustrate the outer cover 36 which is interconnectable to the intermediate frame 44 and lower frame 46 in the same manner described above with reference to the housing assembly 28 embodiment illustrated in FIGS. 1-14. An electronics panel 42 may be mounted on an upper portion of the intermediate frame 44 and may also serve to capture the suspension mounts 22 which extend laterally outwardly from the blower housing 16.

FIGS. 17-20 further illustrate the acoustic housing 52 which is shown as being integrally molded into the lower frame 46 as opposed to the separately mounted arrangement illustrated in FIGS. 3-5 and described above. The acoustic housing 52 shown in FIGS. 17-20 is preferably disposed in spaced relation to the housing assembly 28 on its vertical sides in order to provide a housing gap 58 therebetween. As was described above, the housing gap 58 minimizes the propagation of structure-borne vibration from the acoustic housing 52 to the housing assembly 28.

Referring still to FIGS. 17-20, the acoustic housing 52 includes the inlet chamber 48 fluidly connected to the acoustic chamber 50 which acts as a reactive component 70. The acoustic chamber 50 may include a pair of damped resonators 80 configured as perforated plates 84 backed by porous material 94 as best seen in FIG. 20. The perforated plates 84 are preferably angularly oriented relative to the acoustic velocity in order to produce a grazing flow thereagainst which increases resonator 80 losses. A second compliant-walled reactive tube 72 fluidly connects the acoustic chamber 50 to the blower chamber 62. The reactive tube 72 may be supported on the outlet 32 of the acoustic chamber 50 by a ring of resilient (i.e., foam) material. An acoustic cover 60 best seen in FIGS. 17-18 encloses the acoustic housing 52 and may itself include a plurality of randomly-placed thick sections 68 in order to break up the relatively large constant thickness panel of the acoustic cover 60.

Figure 21:
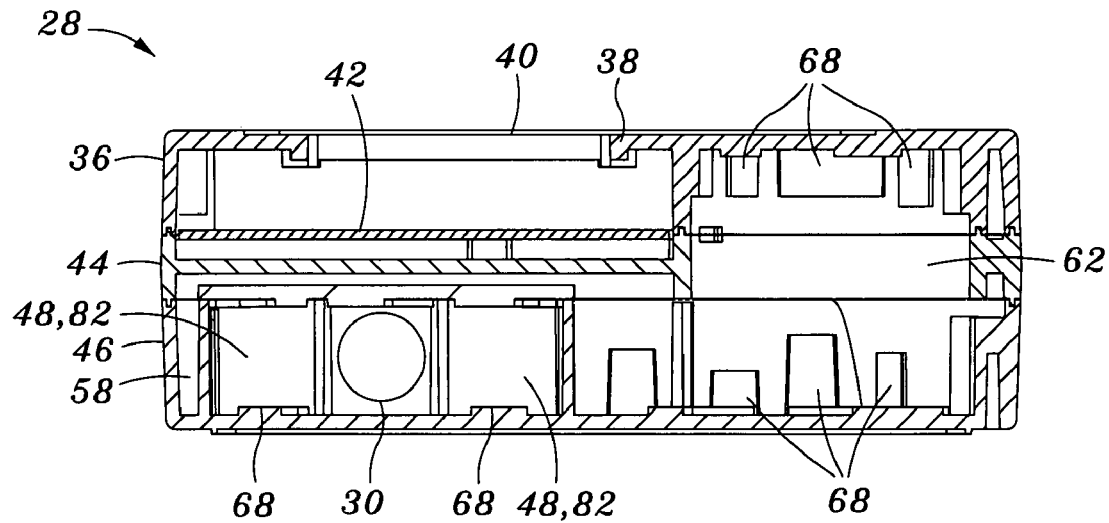
FIG. 21 is a cross sectional view of the housing assembly taken along lines 21-21 of FIG. 16 and illustrating the inlet chamber and lower chamber collectively defined by the outer cover, intermediate frame, and lower frame of the housing assembly.

Referring to FIGS. 19-20, the blower chamber 62 may include a damped resonator 80 configured as a perforated plate 84 backed with porous material 94. The blower chamber 62 itself preferably includes a plurality of thick sections 68 having random shapes and locations. Likewise, the peripheral chamber walls 64 may also include randomly-placed thick sections 68 as best seen in FIG. 21. Each of the reactive components 70, resonators 80, and dissipative elements 92 included in the housing assembly 28 are preferably configured to attenuate different frequency bands. Advantageously, the combination of the various noise attenuation and vibration isolation features minimizes noise level generated by the CPAP device without sacrificing the flow output characteristics of the blower assembly. Furthermore, all of these above-mentioned features are provided in a reduced size such that the CPAP device may be effectively packaged in the tabletop CPAP device similar to that which is disclosed in U.S. Pat. No. 7,195,014.

Referring now to FIG. 23, the humidifier assembly 100 is adapted for use with the housing assembly 28 illustrated in FIGS. 1-22 and is similar in arrangement and function to the humidifier assembly 100 described above with reference to FIG. 14. More specifically, the humidifier assembly 100 is adapted to receive pressurized gas from the outlet 32 of the housing assembly 28. The pressurized gas is drawn downwardly into the reservoir 102 of the humidifier assembly 100 is comprised of the container 122 and the cover assembly 104.

The reservoir 102 is adapted for containing liquid which is vaporized by an electrically-powered heating element 126 disposed on an underside of the tray 124. The heating element 126 is operative to vaporize the liquid which then becomes entrained within the pressurized gas flow and is discharged out of the humidifier assembly 100 for delivery to the patient. A patient hose (not shown) may connect the blower device 12 to a user interface (i.e., nasal mask, nasal prongs). The humidifier assembly 100 includes the control base 132 containing the heat control circuitry 134, humidifier control panel 136 and push-button switches and LED's 144 similar to that described above for regulating the heating element 126.

Operation of the silencer 10 in the two exemplary embodiments will now be described with reference to the drawings. Initially, power is supplied to the motor blower unit 14 causing the impeller to rotate and thereby drawing air into the housing assembly 28 inlet 30 illustrated in FIGS. 4 and 18. The air enters the reactive tube 72 disposed within the inlet chamber 48. The compliant walls of the reactive tube 72 respond to the acoustic energy which allows the spaced (i.e., cavity volume) surrounding the reactive tube 72 to act as a resonator 80. The inlet chamber 48 may include perforated plates 84 back by foam in the configuration illustrated in FIG. 20 to lower the Q of the inlet chamber 48 and thereby broaden the frequency band. The angled or beveled trailing end 78 of the reactive tube 72 further broadens the attenuation bandwidth.

After exiting the inlet chamber 48, the acoustic velocity grazes the perforated plate(s) 84 located within the acoustic chamber 50 to attenuate the acoustic energy. Dissipative porous material 94 disposed behind the perforated plates 84 provides an energy-absorbing feature. Depending upon the configuration, the flow path 34 defines a right-angle turn in the horizontal and/or vertical plane. For the configuration shown in FIGS. 1-14, the acoustic chamber 50 may comprise the first and second chambers 54, 56.

The perforated plate 84 in the first chamber 54 is preferably disposed in angled orientation to the acoustic flow and has dissipative porous material 94 (i.e., foam) disposed therebehind. The second chamber 56 includes a second reactive tube 72 extending into the blower chamber 62 and defining the cavity volume 82 therearound to act as a resonator 80. The perforated plate 84 in the second chamber 56 is foam-backed to provide energy-absorbing attenuation.

As best seen in FIG. 13, the housing gap 58 between the acoustic housing 52 and the housing assembly 28 isolates structure-borne vibration from the housing assembly 28 (e.g., CPAP enclosure). Randomly-placed thick sections 68 in the chamber walls 64 of the inlet chamber 48, acoustic chamber 50 and blower chamber 62 prevent single-frequency, large-amplitude resonance of such chamber walls 64 and instead induces multiple frequency responses each having a relatively small amplitude. The perforated plate 84 in the blower chamber 62 further attenuates and dissipates acoustic energy due in part to the porous material 94 disposed behind the perforated plate 84.

If included with the blower device 12, the humidifier assembly 100 generates vapor for entrainment into the flow of pressurized gas produced by the motor blower unit 14. Such pressurized gas is discharged out of the outlet 32 of the housing assembly 28 and enters the humidifier inlet 118. The humidifier assembly 100 is arranged to provide a tortuous or complex flow path 34 for the pressurized gas to further attenuate acoustic energy contained with the flow. Liquid contained within the reservoir 102 is heated and vaporized by the heating element and thereby humidifies the pressurized gas. The humidified pressurized gas is then discharged from the humidifier outlet 120 for delivery to the patient such as via a patient hose extending to a nasal mask, nasal prongs or other suitable user interface.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A silencer for a blower device, the silencer comprising:
 a housing assembly having a flow path passing therethrough and including an inlet chamber, an acoustic chamber and a blower chamber, each chamber being defined by chamber walls and having an inlet, an outlet and including at least one of the following:

a reactive component configured as a compliant-walled reactive tube at least partially disposed within the chamber;

a resonator configured as at least one of a perforated plate and a cavity volume; and a dissipative element comprising porous material sized and configured to at least partially occupy the cavity volume bounded by the perforated plate and the chamber walls, wherein the acoustic chamber comprises each of the reactive component, the resonator, and the dissipative element.

2. The silencer of claim 1, wherein the reactive component comprises a pair of the reactive tubes, one of the reactive tubes extending through the inlet chamber, the other one of the reactive tubes extending from an outlet of the acoustic chamber to an inlet of the blower chamber.

3. The silencer of claim 2, wherein the reactive tubes having differing lengths such that different frequency bands are attenuated thereby.

4. The silencer of claim 2, wherein the inlet chamber includes a pair of perforated plates disposed longitudinally on opposed sides of the reactive tube.

5. The silencer of claim 4, wherein:

the inlet chamber includes a pair of perforated plates disposed on opposed longitudinal sides of the reactive tube; and each one of the perforated plates having porous material disposed therebehind to lower the quality factor (Q) of the inlet chamber for broadening the attenuation bandwidth of the volume cavity.

6. The silencer of claim 1, wherein at least one of the acoustic and blower chambers includes at least one perforated plate oriented in angled relationship to the flow path.

7. The silencer of claim 1, wherein the perforated plate has a front face and a back face, the porous material being disposed in abutting contact with the back face.

8. The silencer of claim 1, wherein the reactive component, resonator and dissipative element are each configured to attenuate different frequency bands.

9. The silencer of claim 1, wherein:

the housing assembly includes a plurality of perforated plate resonators each having a plurality of apertures of uniform size extending therethrough; and the apertures in each of the perforated plates being sized such that each perforated plate attenuates a different frequency band.

10. The silencer of claim 1, wherein at least one chamber wall includes a locally thick section configured to prevent vibration of the chamber wall at a single resonant frequency.

11. The silencer of claim 1, wherein:

the chamber walls of the inlet chamber, acoustic chamber and blower chamber each include a plurality of thick sections; and each of the thick sections being sized and configured to generate a differing high frequency resonance.

12. The silencer of claim 1, wherein the inlet chamber and acoustic chamber are incorporated into an acoustic housing configured to be separately mountable within the housing assembly in spaced relation thereto.

13. The silencer of claim 12, wherein the acoustic housing is supported in the housing assembly by at least one suspension mount adapted to prevent the transmission of structure-borne noise from the acoustic chamber to the housing assembly.

14. The silencer of claim 1, wherein:

the acoustic chamber comprises first and second chambers;

the first chamber including a perforated plate having porous material disposed therebehind; and the second chamber having a reactive tube extending therefrom into the blower chamber and defining a cavity volume, the second chamber further including a perforated plate having porous material disposed therebehind.

15. The silencer of claim 1, wherein the reactive tube has a uniform cross section and being sized and configured to minimize a velocity of the flow passing therethrough.

16. The silencer of claim 15, wherein the cross sectional area of the reactive tube is such that the flow velocity is maintained at less than about Mach 0.1.

17. The silencer of claim 1, wherein each one of the reactive tubes has a leading end and a trailing end, the trailing end being beveled.

18. The silencer of claim 1, wherein the inlet of the inlet chamber is out of line-of-sight with the outlet of the acoustic chamber.

19. The silencer of claim 1, wherein the porous material is open cell foam.

20. The silencer of claim 1, wherein the flow path between the inlet chamber and the blower chamber includes at least one ninety-degree turn.

21. The silencer of claim 1, wherein the flow path between the inlet chamber and the blower chamber includes at least two right-angle turns each defining a turning plane, the right-angle turns being oriented in non-planar relationship to one another.

22. A humidifier assembly for a blower device having a blower chamber, the humidifier assembly comprising:

a reservoir including a container and a cover assembly engageable to the container, the container being adapted for containing a liquid, the cover assembly having a humidifier inlet and humidifier outlet; and a heating element disposed in contacting relationship with the container and being operative to vaporize the liquid, wherein the humidifier inlet is in fluid communication with the blower chamber such that compressed air produced by the blower device enters the humidifier inlet and entrains vaporized liquid prior to discharge from the humidifier outlet, and wherein the blower device further comprises an acoustic chamber, comprising:

a reactive component configured as a compliant-walled reactive tube at least partially disposed within the chamber;

a resonator configured as at least one of a perforated plate and a cavity volume; and a dissipative element comprising porous material sized and configured to at least partially occupy the cavity volume bounded by the perforated plate and the chamber walls.

* * * * *